US011589879B2

(12) United States Patent
Nino

(10) Patent No.: US 11,589,879 B2
(45) Date of Patent: Feb. 28, 2023

(54) DISPOSABLE INTEGRATED SPEED REDUCTION AND GEARLESS HIGH TORQUE DEVICE

(71) Applicant: ECA Medical Instruments, Inc., Newbury Park, CA (US)

(72) Inventor: John Nino, Newbury Park, CA (US)

(73) Assignee: ECA Medical Instruments, Inc., Thousand Oaks, CA (US)

( * ) Notice: Subject to any disclaimer, the term of this patent is extended or adjusted under 35 U.S.C. 154(b) by 311 days.

(21) Appl. No.: 16/761,495

(22) PCT Filed: Nov. 2, 2018

(86) PCT No.: PCT/US2018/059061
§ 371 (c)(1),
(2) Date: May 4, 2020

(87) PCT Pub. No.: WO2019/090151
PCT Pub. Date: May 9, 2019

(65) Prior Publication Data
US 2020/0305893 A1   Oct. 1, 2020

Related U.S. Application Data

(60) Provisional application No. 62/580,816, filed on Nov. 2, 2017.

(51) Int. Cl.
*A61B 17/16* (2006.01)
*A61B 90/00* (2016.01)
*A61B 17/00* (2006.01)

(52) U.S. Cl.
CPC .......... *A61B 17/1624* (2013.01); *A61B 90/03* (2016.02); *A61B 2017/00831* (2013.01); *A61B 2090/031* (2016.02); *A61B 2560/0285* (2013.01)

(58) Field of Classification Search
CPC .......... A61B 17/1624; A61B 2090/037; A61B 2090/031
See application file for complete search history.

(56) References Cited

U.S. PATENT DOCUMENTS 5,269,733 A   12/1993   Anthony, III
5,993,454 A   11/1999   Longo
(Continued)

FOREIGN PATENT DOCUMENTS

| EP | 2184138 | 5/2010 |
|---|---|---|
| WO | 2017062071 | 4/2017 |
| WO | 2017062651 | 4/2017 |

OTHER PUBLICATIONS

Search Report and Written Opinion of International Patent Application No. PCT/US2018/059061; dated Feb. 7, 2019.
(Continued)

*Primary Examiner* — Christian A Sevilla
(74) *Attorney, Agent, or Firm* — Ferguson Case Orr Paterson

(57) ABSTRACT

An integrated disposable rotational speed reduction assembly having a shaft assembly, a housing, an output assembly, and a plurality of planetary gears each having a plurality of gear teeth. The shaft assembly is configured to cause rotation of the planetary gears with a sun gear. The rotation of the planetary gears is configured to cause rotation of an output shaft, with a reduction of rotational speed relative to the rotation of the shaft assembly.

26 Claims, 17 Drawing Sheets

(56) References Cited

U.S. PATENT DOCUMENTS

| | | | |
|---|---|---|---|
| 7,762,164 B2* | 7/2010 | Nino | B25B 23/1427 |
| | | | 81/475 |
| 2008/0287247 A1* | 11/2008 | Pusateri | B25B 21/00 |
| | | | 81/436 |
| 2011/0073337 A1 | 3/2011 | Milbourne | |
| 2013/0226192 A1 | 8/2013 | Nino | |
| 2013/0276598 A1 | 10/2013 | Ivinson | |
| 2013/0303330 A1* | 11/2013 | Stevens | A61M 25/0113 |
| | | | 475/349 |
| 2015/0047463 A1 | 2/2015 | Hofmann | |
| 2015/0148176 A1* | 5/2015 | Schroeder | A61B 17/1622 |
| | | | 464/33 |
| 2017/0232592 A1* | 8/2017 | Nino | B25B 23/141 |
| | | | 81/475 |
| 2017/0361437 A1 | 12/2017 | Nino | |

OTHER PUBLICATIONS

EPO Commnunication Pursuant to Rules 70(2) and 70a(2) EPC of Application No. 18872761.4 dated Jul. 27, 2021.
EPO Supplementary Search Report of Application No. 18872761.4 dated Jul. 8, 2021.

* cited by examiner

A-A

B-B

C-C

E-E

D-D

ND GEARLESS HIGH
DISPOSABLE INTEGRATED SPEED REDUCTION AND GEARLESS HIGH TORQUE DEVICE

CROSS-REFERENCE TO RELATED APPLICATIONS

This is national phase application of International Application No. PCT/US18/059061, filed on Nov. 2, 2018, which claims the benefit of U.S. Provisional Patent Application No. 62/580,816 filed Nov. 2, 2017. Each of the applications referenced in this paragraph is incorporated by reference in its entirety as if fully set forth herein.

TECHNICAL FIELD

This disclosure relates generally to single use rotational speed reduced torque limiting devices.

BACKGROUND

Power tools are used for some applications in the medical industry. Such power tools can provide torque to a workpiece while also providing higher rotational rates than can be provided with manually driven tools. Torque-limiting systems can be utilized with medical power tools, either as an additional attachment provided in-line between the power tool and the workpiece or as internalized systems within the power tool itself. Reusable torque-limiting systems need to be sterilized between uses and typically must be serviced and recalibrated periodically to ensure performance within specifications. Disposable torque-limiting systems are an alternative to the reusable systems. Once the torque-limiting system has been used, it is discarded.

Tools used in different industries operate at many different speeds, and controlling the speed of operation is sometimes necessary. Disposable torque-limiting devices can be susceptible to premature failure if utilized with high speed power tools. The need for carefully controlled speed of resecting tools often used in surgery is well known. The need to control force applied to fasteners, implants and the like during medical procedures is well known. Tools used during medical procedures must meet a predetermined level of sterilization. The financial and societal costs of infections caused by improperly sterilized items used during surgery are significant. Maintaining and sterilizing speed reduced powered tools used during medical procedures adds to the cost of health care.

Thus there is a need for disposable torque-limiting systems that can be utilized with medical power tools to limit applied torque at higher rotational speeds and remain in specification over a predetermined number of actuations. The disclosure is directed to these and other important needs.

DISCLOSURE

Many rotational tools (e.g. drills) operate at very high velocities, and it is sometimes necessary to reduce or limit how fast such tools spin. In the medical field, torque limiting devices in the operational theater are useful to reduce variables associated with resection and fastening medical devices. However, unrestricted high-speed device operation may add unnecessary risk variables to a procedure.

According to aspects of some exemplary implementations of the disclosure, the disclosure provides integrated rotational speed reduction assemblies having a shaft assembly, a housing, an output assembly, and a plurality of planetary gears each having a plurality of gear teeth. In some implementations of the integrated rotational speed reduction assemblies, the shaft assemblies can have a sun gear with a plurality of gear teeth, the shaft assembly can provide for the mating between the housing and the output assembly via one or more retaining features provided on the shaft assembly. In some implementations, the output assembly can have a plurality of pin guides, with each pin guide mating with one of the plurality of planetary gears to prevent relative axial movement between each mated pin guide and planetary gear but allowing for relative axial rotation between each mated pin guide and planetary gear; the housing can have a gear ring of a plurality of gear teeth disposed on an interior surface of the housing, with the gear ring configured to engage with the gear teeth of the planetary gears, and at least a portion of the output assembly can be configured to rotate in response to rotation of the shaft assembly, via engagement between the sun gear and the planetary gears, engagement between the planetary gears and the gear ring.

According to aspects of some exemplary implementations of the disclosure, methods of reducing rotational velocity of a tool include a step of engaging a tool with an integrated rotational speed reduction assembly as it is described in any of the exemplary implementations throughout this application. In some implementations, the methods can include a step of operating the tool once it is engaged with the integrated rotational speed reduction assembly.

DRAWINGS

The summary, as well as the following detailed description, is further understood when read in conjunction with the appended drawings. For the purpose of illustrating the disclosure, there are shown in the drawings exemplary implementations of the disclosure, however, the disclosure is not limited to the specific methods, compositions, and devices disclosed. In addition, the drawings are not necessarily drawn to scale.

Figure 1:
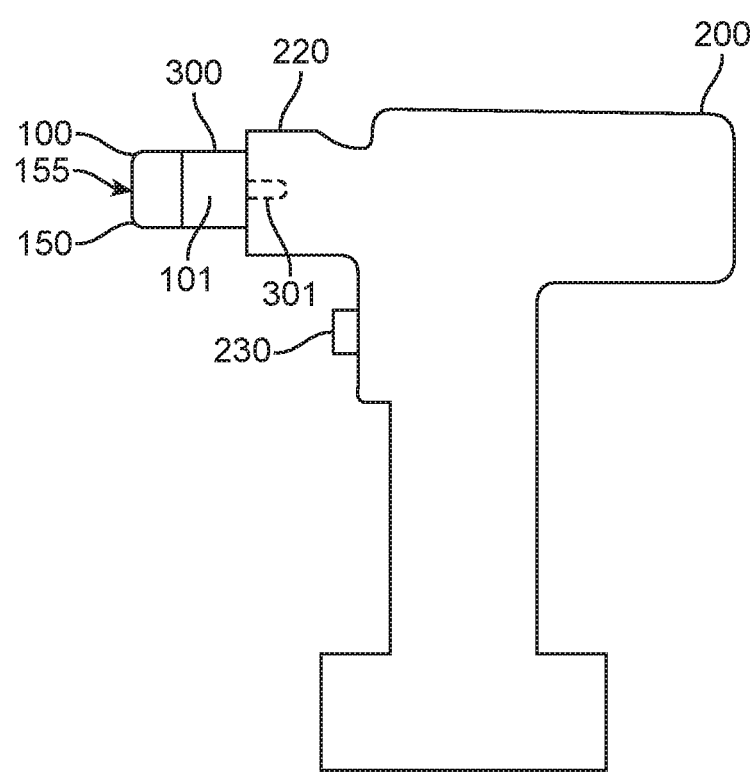
FIG. 1 is a schematic illustration of a side view of an exemplary implementation of a rotational speed reduction device.

All reference numerals, designators, and call-outs in the figures are hereby incorporated by this reference as if fully set forth herein. The failure to number an element in a figure is not intended to waive any rights, and unnumbered references may also be identified by alpha characters in the figures.

FURTHER DISCLOSURE

Some aspects of the disclosure will now be described in further detail with reference to the drawings, wherein like reference numbers refer to like elements throughout, unless specified otherwise. Certain terminology is used in the following description for convenience only and is not limiting.

For the purpose of illustrating the subject matter, there are shown in the drawings exemplary implementations of the subject matter; however, the presently disclosed subject matter is not limited to the specific methods, devices, and systems disclosed. In addition, the drawings are not necessarily drawn to scale.

The present disclosure may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular exemplary implementations by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to apparatuses and methods of using said apparatuses. That is, where the disclosure describes or claims a feature or embodiment associated with an apparatus or a method of using an apparatus, it is appreciated that such a description or claim is intended to extend these features or embodiment to exemplary implementations in each of these contexts (i.e., apparatuses, methods of making, and methods of using).

In the present disclosure, the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another exemplary implementation. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the disclosure which are, for clarity, described herein in the context of separate exemplary implementations, may also be provided in combination in a single implementation. That is, unless obviously incompatible or specifically excluded, each individual exemplar is deemed to be combinable with any other exemplar(s) and such a combination is considered to be another exemplar. Conversely, various features of the disclosure that are, for brevity, described in the context of a single exemplar, may also be provided separately or in any sub-combination. Finally, while an exemplar may be described as part of a series of steps or part of a more general structure, each said step may also be considered an independent exemplar in itself, combinable with others.

The transitional terms "comprising," "consisting essentially of," and "consisting" are intended to connote their generally accepted meanings in the patent vernacular; that is, (i) "comprising," which is synonymous with "including," "containing," or "characterized by," is inclusive or open-ended and does not exclude additional, un-recited elements or method steps: (ii) "consisting of" excludes any element, step, or ingredient not specified in the claim; and (iii) "consisting essentially of" limits the scope of a claim to the specified materials or steps "and those that do not materially affect the basic and novel characteristic(s)." Exemplars described in terms of the phrase "comprising" (or its equivalents), also provide, as exemplars, those which are independently described in terms of "consisting of" and "consisting essentially" of.

When a list is presented unless stated otherwise, it is to be understood that each individual element of that list, and every combination of that list, is a separate exemplar. For example, a list of exemplars presented as "A, B, or C" is to be interpreted as including the exemplars, "A," "B," "C," "A or B," "A or C," "B or C," or "A, B, or C."

Throughout this specification, words are to be afforded their normal meaning, as would be understood by those skilled in the relevant art. However, so as to avoid misunderstanding, the meanings of certain terms will be specifically defined or clarified.

Figure 2:
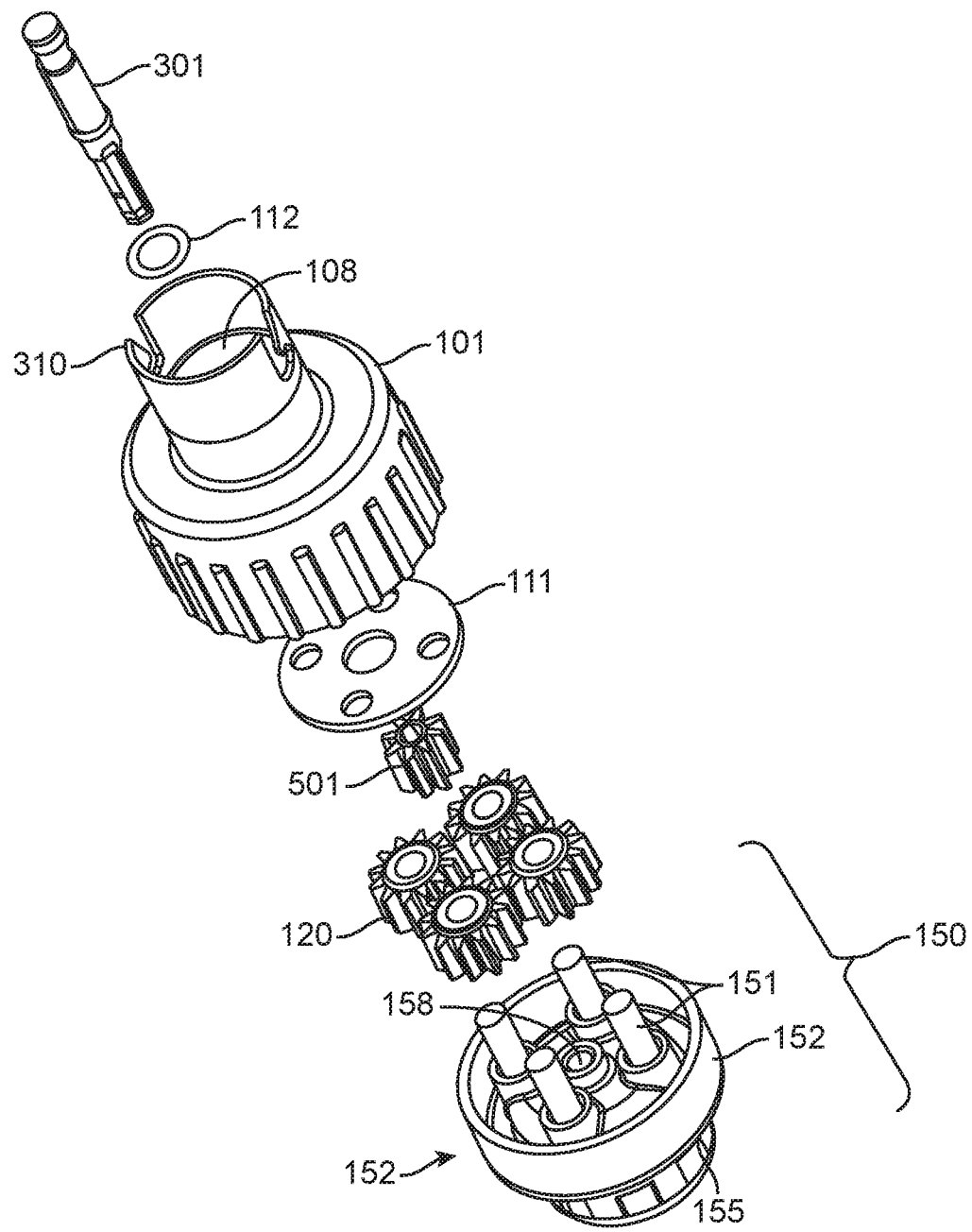
FIG. 2 is an exploded view of an exemplary implementation of an integrated rotational speed reduction assembly.
Figure 3:
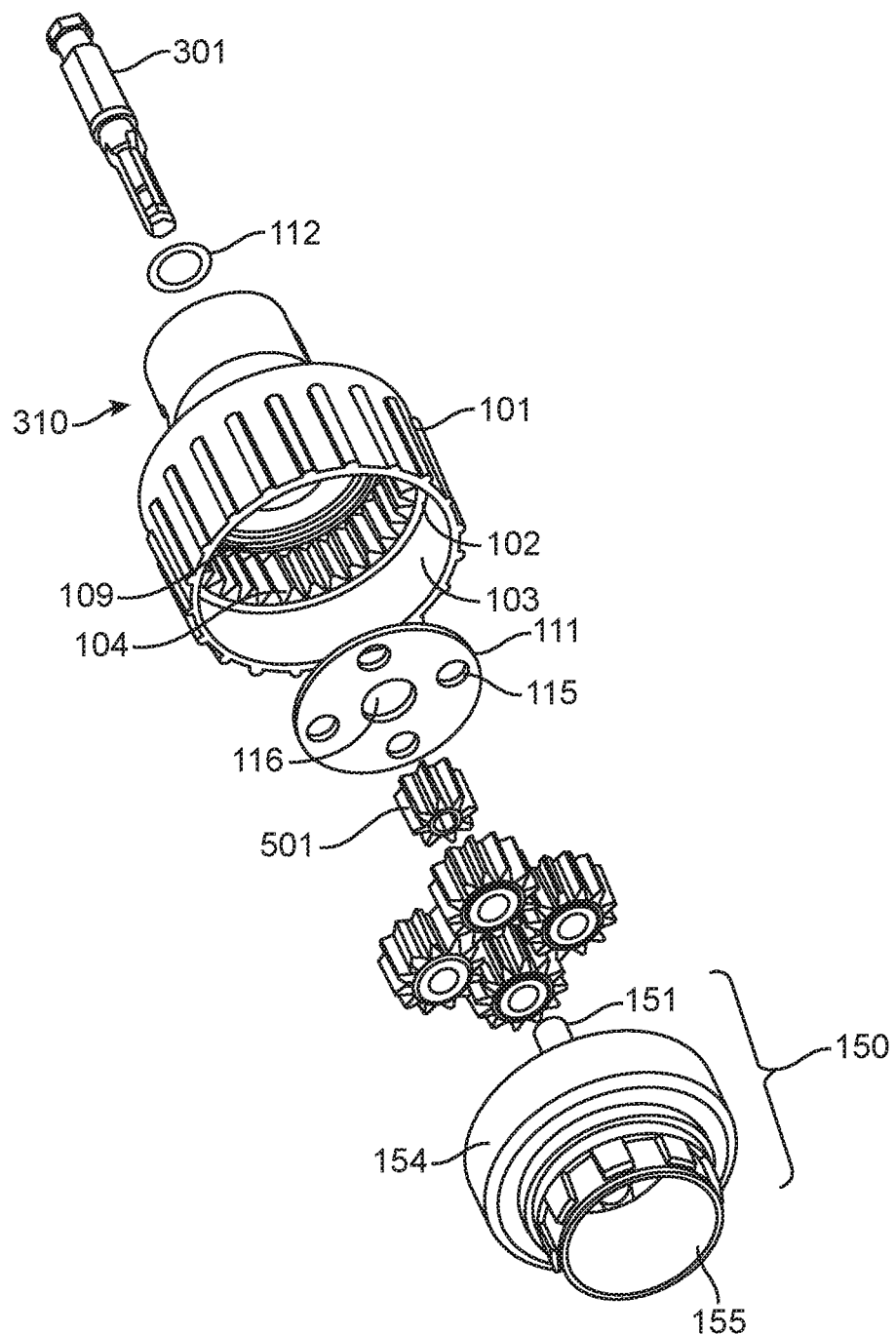
FIG. 3 is an exploded view from a different angle of the integrated rotational speed reduction assembly shown in FIG. 2.
Figure 4:
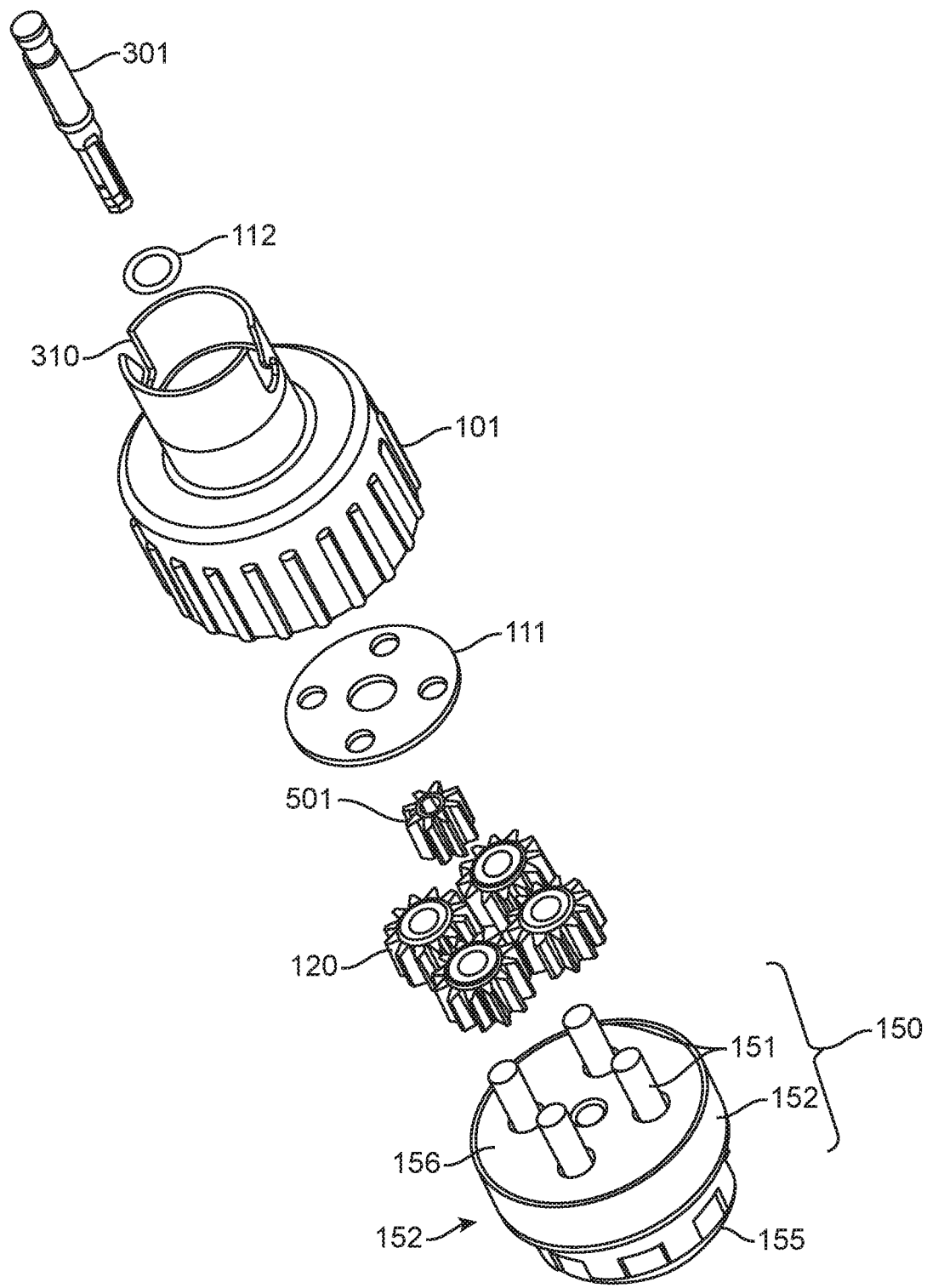
FIG. 4 is an exploded view of an exemplary implementation of an integrated rotational speed reduction assembly.
Figure 5:
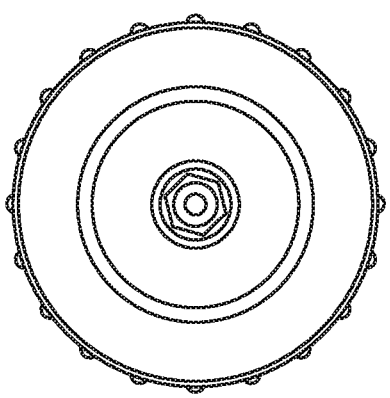
FIG. 5 is a top view of an exemplary implementation of an integrated rotational speed reduction assembly.
Figure 6:
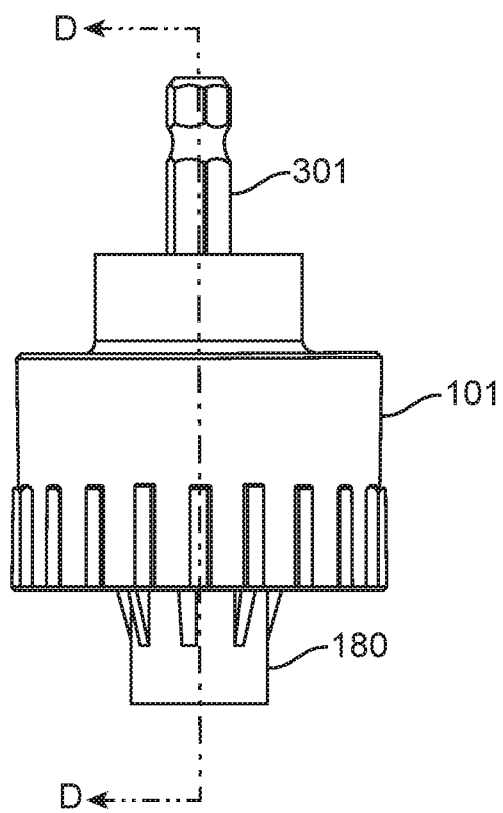
FIG. 6 is a side view of the integrated rotational speed reduction assembly shown in FIG. 5.
Figure 7:
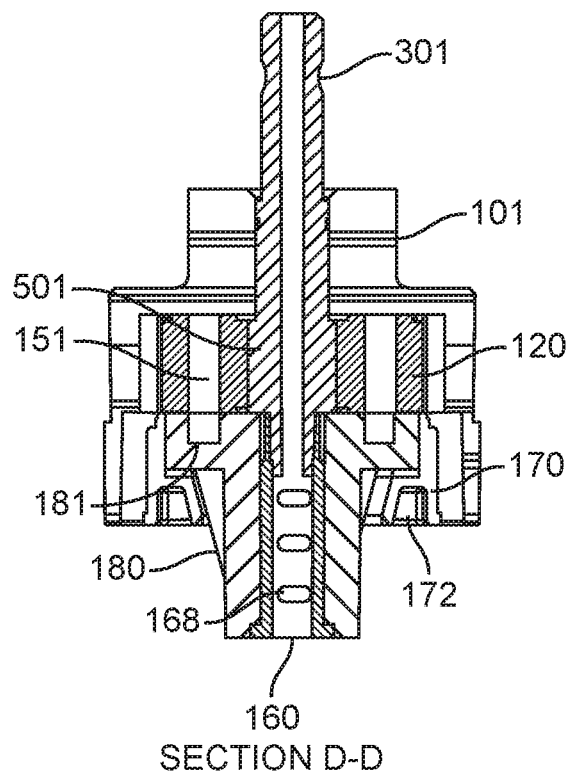
FIG. 7 is a cross-sectional view of the integrated rotational speed reduction assembly shown in FIGS. 5 and 6.
Figure 9:
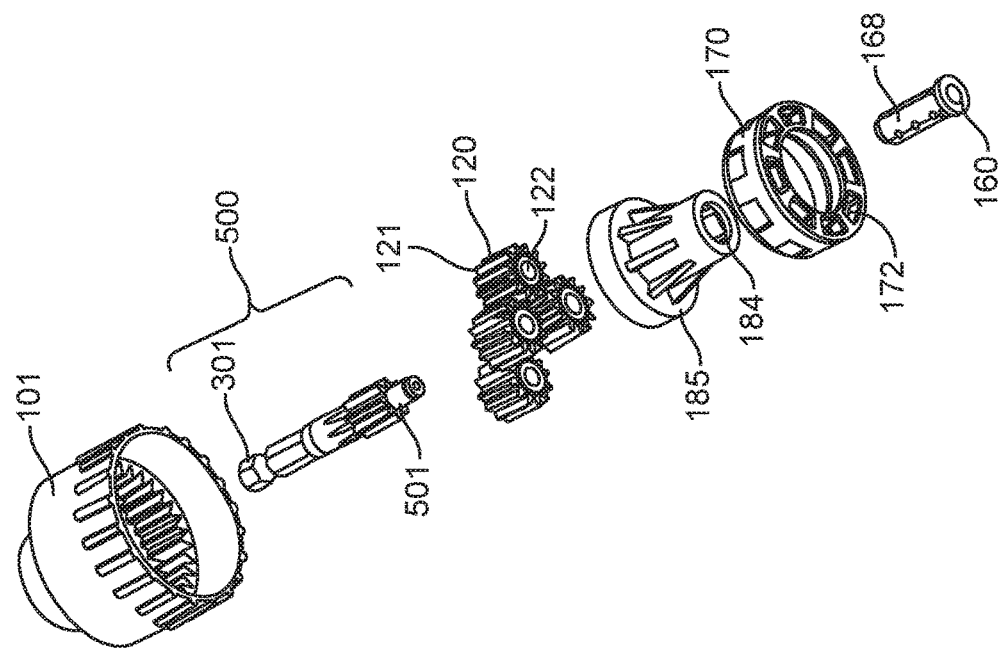
FIG. 9 is an exploded view from a different angle of the integrated rotational speed reduction assembly shown in FIGS. 5-8.
Figure 8:
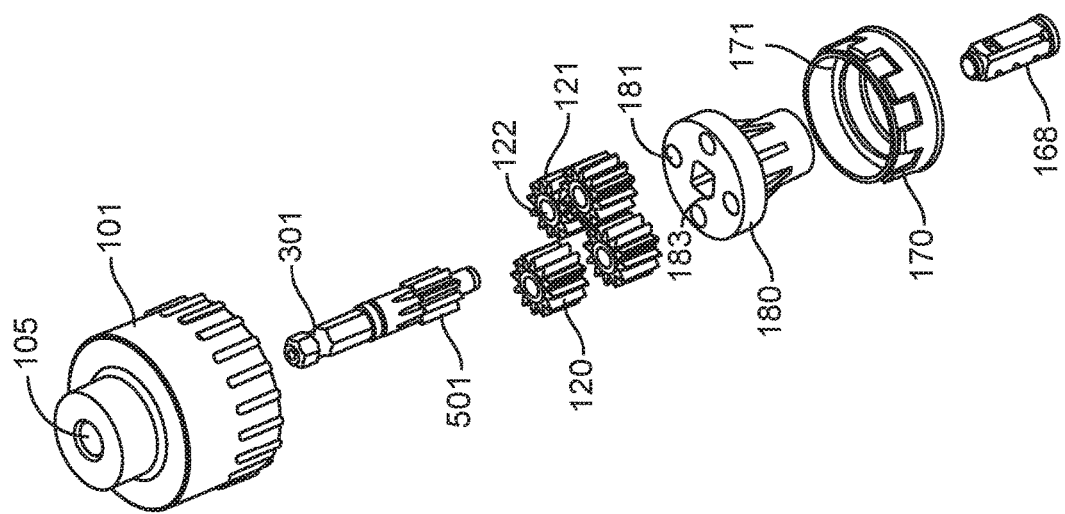
FIG. 8 is an exploded view of the integrated rotational speed reduction assembly shown in FIGS. 5-7.

FIG. 1 depicts aspects of an implementation of a medical power tool system incorporating implementations of an integrated rotational speed reduction assembly 100. A medical power tool 200 with one or more actuation buttons 230 and an output mechanism 220 can be used. Output mechanism 220 can include a recessed opening that contains the output connection. Many standard types of output connections are known to those of skill in the art, including AO small, AO large, Trinkle, Hudson, Harris, and Zimmer. Integrated rotational speed reduction assembly 100 has a housing 101 with an interface system 300, which can be connected to output mechanism 220 and affixed in place such that the output connection is connected to a drill connection shaft 301 that is part of a shaft assembly 500 within the integrated rotational speed reduction assembly 100. Housing 101 can be provided with an interface system 300 having a retaining feature 310 that is used to lock the housing 101 in place relative to the output mechanism 220, such that the housing 101 does not rotate, but drill connection shaft 301 may rotate as it is driven by the medical power tool 200. A quick-turn retaining feature 310 is depicted in FIGS. 2-4, but alternative retaining features such as helical threading or fasteners could also be used. Retaining features of interface system 300 have been omitted from FIGS. 5-9 and 12-13 for illustrative purposes, but any suitable retaining feature described herein could be provided on housing 101. Drill connection shaft 301, also referred to herein as a drive shaft, can be configured with a variety of end profiles and connection types in order to interface with the output mechanism utilized in the particular power tool 200 being used in the system. Actuation button 230 can be utilized by a user to activate an internal motor of the power tool 200 (not shown) that transmits rotational force to output mechanism 220 and causes the mechanism to rotate.

Housing 101 is configured to interface with an output assembly 150 to enclose internal planetary gear components and form an integrated rotational speed reduction assembly 100. Housing 101 is mated to the output assembly 150. The housing 101 and output assembly 150 can be mated with a snap-fit connection, welded, or connected with another suitable manner, provided that at least any planet carrier portion of the output assembly 150 can rotate relative to the housing 101, as described more fully elsewhere herein. In some exemplary implementations, the housing 101 and output assembly 150 are held together by the drill connection shaft 301, which has retaining features 505/506 which interface with portions of the housing 101 and the output assembly 150 to hold them in close proximity, as described more fully elsewhere herein. At a distal end 155 of the output assembly 150, a workpiece interface is included to provide for transfer of rotational torque to a workpiece (not shown). In FIGS. 2-4, 12 and 13 the workpiece interface is illustrated conceptually as a stepped profile around the outer surface of the distal end 155, but in other implementations the workpiece interface can be a tip connection 160 disposed within a central portion of the distal end 155 or any other element that is rigidly fixed to rotate with the planet carrier portion of the output assembly 150. The tip connection 160 can be configured to interface with a workpiece or another workpiece-engaging component (not shown or further described herein). Tip connection 160 can be implemented as one of many connection types, including a female AO type connection, AO small, AO large, Trinkle, Hudson, Harris, Zimmer, ¼-inch square, socket wrenches, or other profiles. In some implementations, tip connection 160 can be configured with a workpiece-engaging profile for direct use on a workpiece or fastener. Some suitable configurations for tip connection 160 and workpiece engaging tips are disclosed in U.S. Patent Publication No. US2013/0226192 A1, which is incorporated by reference herein in its entirety. In some implementations tip connection 160 can also be configured to accept a keyed or keyless drill chuck with jaws that can clamp a variety of tools including drills and drivers.

Figure 11:
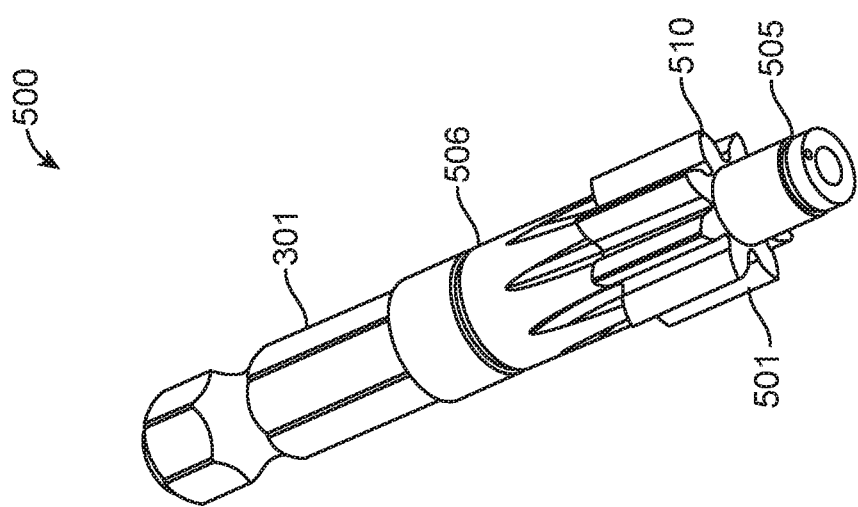
FIG. 11 is a perspective view of aspects of an exemplary implementation of an integrated rotational speed reduction assembly.
Figure 10:
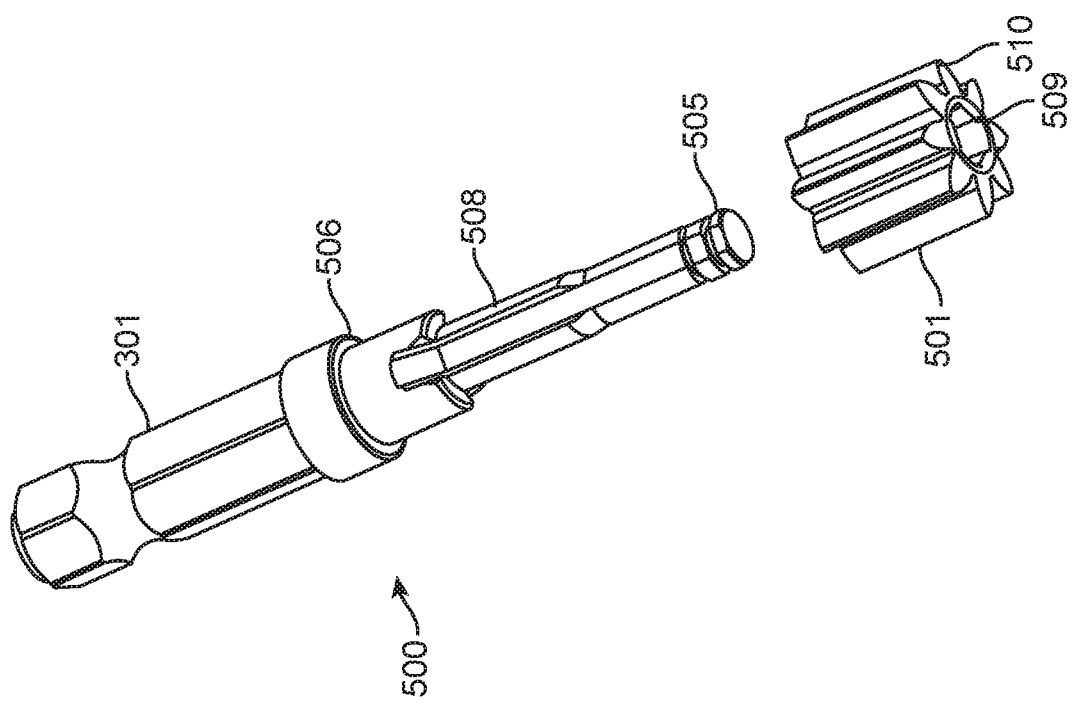
FIG. 10 is an exploded view of aspects of an exemplary implementation of an integrated rotational speed reduction assembly.
Figure 12:
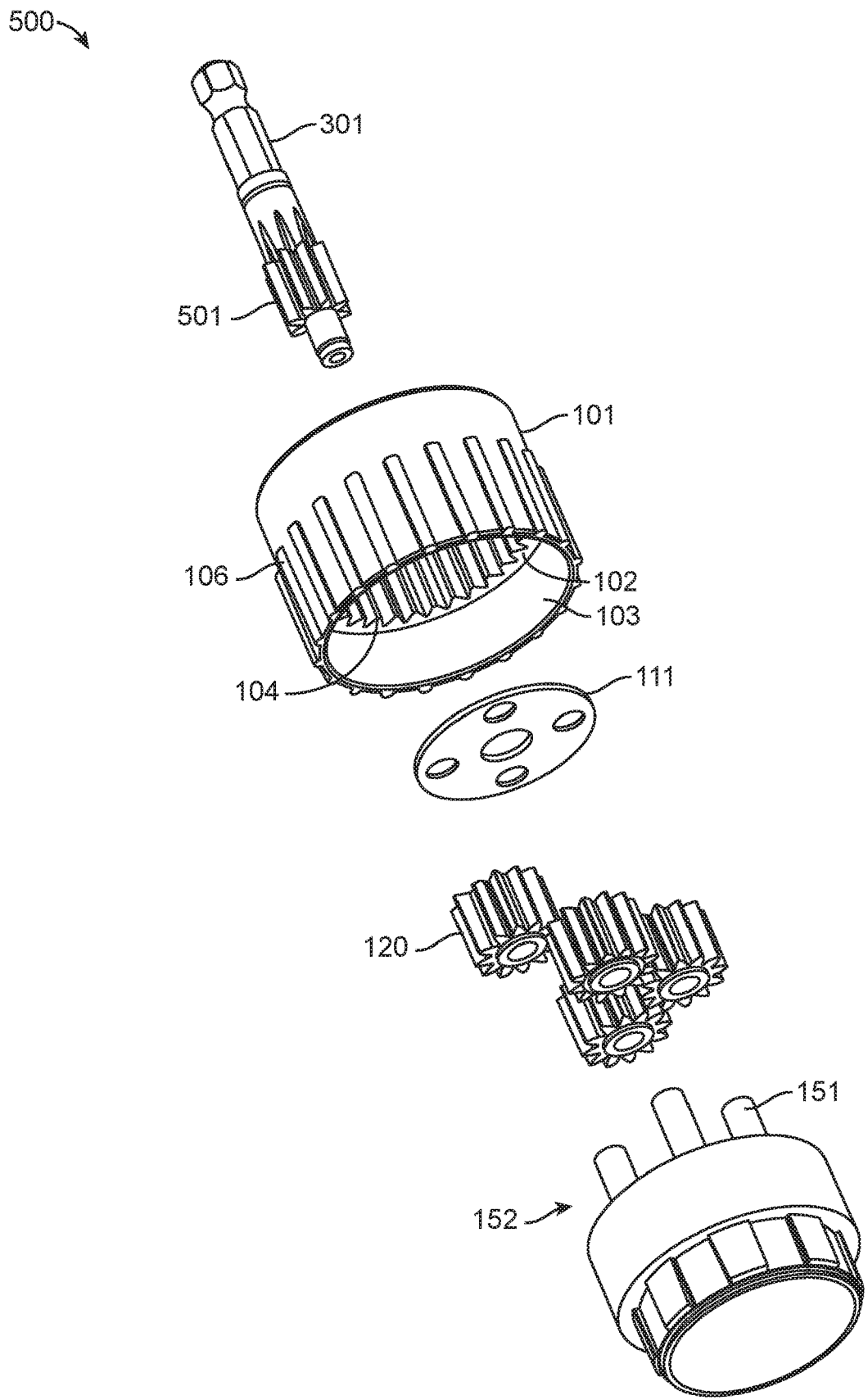
FIG. 12 is an exploded view of an exemplary implementation of an integrated rotational speed reduction assembly.
Figure 13:
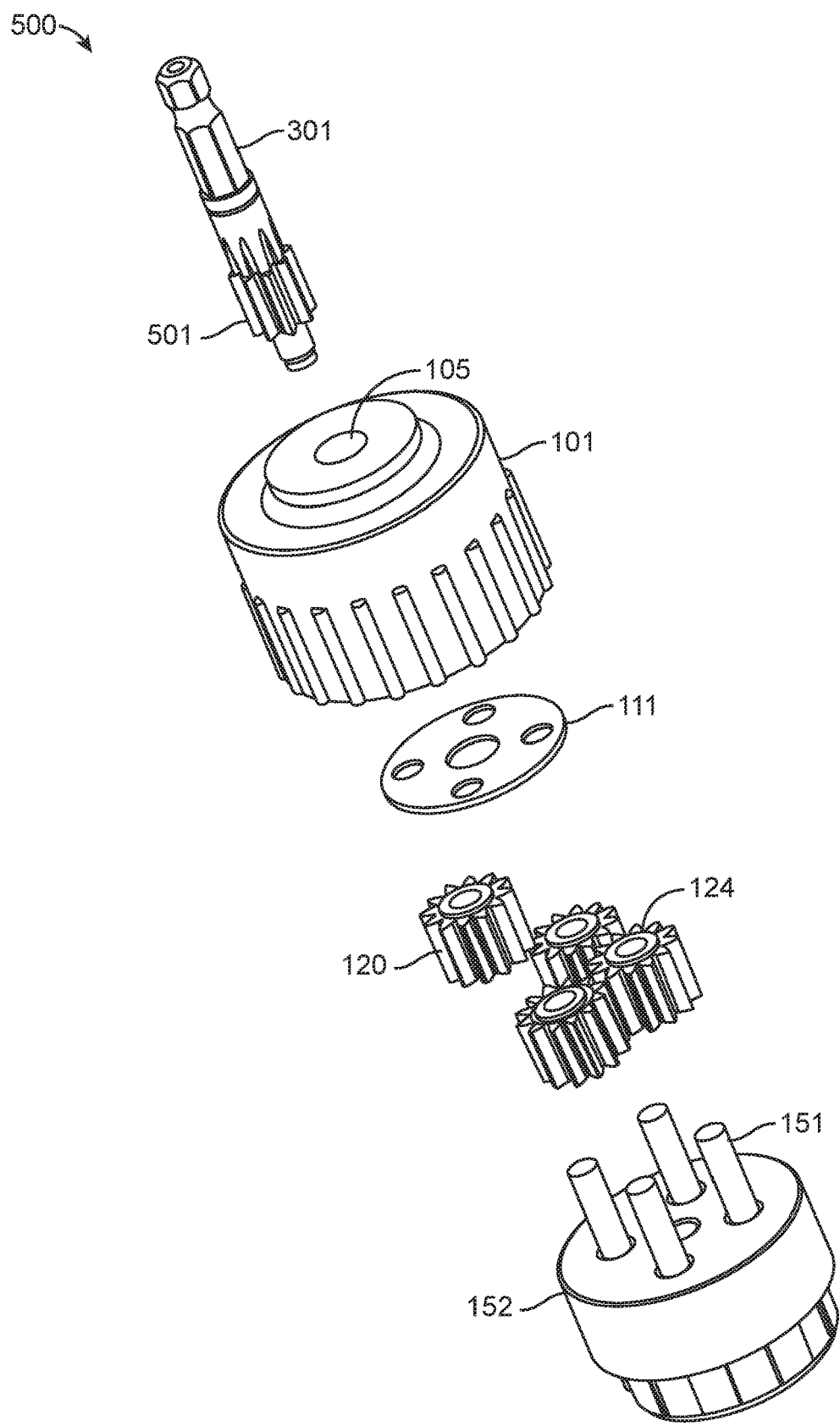
FIG. 13 is an exploded view from a different angle of the integrated rotational speed reduction assembly shown in FIG. 12.

In some implementations a shaft assembly 500 is configured to receive torque input to the integrated rotational speed reduction assembly 100 via the drill connection shaft 301. Some implementations of shaft assembly 500 are shown in FIGS. 10 and 11. The shaft assembly 500 can be formed as a singular piece, or in the alternative, it may be an assembly of multiple pieces. The shaft assembly 500 may be solid or hollow. The shaft assembly 500 may be solid throughout, hollow throughout, or solid in one or more locations and hollow in one or more locations. The shaft assembly 500, sun gear and/or planetary gears may include various materials, such as, but not limited to, metals, plastics, or a combination of metals and plastics. It may be made of metals, such as, but not limited to stainless steel, aluminum, or other metal alloys. In a non-limiting exemplary implementation, the shaft may be made of SAE 316 grade stainless steel. The shaft assembly 500, sun gear and/or planet gears may also be made of plastics, such as, but not limited to high-density polyethylene, low-density polyethylene, polyvinyl chloride, polypropylene, acrylonitrile butadiene styrene, polycarbonate, polyurethane, maleimide, bis-maleimide, melamine formaldehyde, polyetheretherketone, polymethyl methacrylate, polytetrafluoroethylene (PTFE), fluorinated ethylene propylene (FEP), polyacetals (Delrin, Celcon), aliphatic and amorphous grades of nylon polyamides, polymethylpentene, polypropylenes, or a combination of one or more of plastics in this list. The selection of materials may, in part, be associated with the single use cycle requirements of a device.

The shaft assembly 500 can provide for the mating between housing 101 and output assembly 150 through the incorporation of retaining features 505/506. Retaining features 505/506 may be raised edges, slits that snap-fit with raised features on the housing 101 or the output assembly 150, slits or holes that are configured to hold retaining rings or cotter pins, or other systems known in the art that can serve to prevent relative axial movement between the retaining features 505/506 and the corresponding component. In some exemplary implementations a low friction spacer 112 is disposed between a raised lip retaining feature 506 and a surface 108 of the housing 101. The retaining features serve to provide retention of the housing 101 and the output assembly 150 within close proximity of each other, retaining the housing 101 and the output assembly 150 between the two retaining features 505/506, as shown in the Figures. Shaft assembly 500 includes a sun gear 501 with a plurality of gear teeth 510.

In some instances one or more of the drive shaft 301, the sun gear 501, and at least one planet gear 120 are constructed of a material which is frangible or will otherwise fail after a predetermined number of cycles. A cycle for purposes of understanding the exemplar is the distance to complete one rotation of one of the drive shaft and output assembly 150.

In some preferred implementations, any fragments of the one or more of the drive shaft 301, the sun gear 501, and at least one planet gear 120 that result from frangibility or other failure will be retained within the internal cavity of the housing 101.

Preordained failure is used as an aspect of systems and methods disclosed herein to render the disposable device inoperable (within its use parameters) after a predetermined number of use cycles. In the medical arena, single use tools benefit from lower cost materials which are suitable for limited use cycles. Tool construction for a single use device also allows for designs which may have cavities and portions not amenable to subsequent re-sterilizing, thus further providing opportunity for a reduction in health care costs. Risks associated with the improper reuse of single use or disposable tools include but are not limited to contamination, infection, failure during reuse, out of specification performance, damage to the mechanism during attempted re-sterilization. In some instances, about 500 cycles at a predetermined force of Newton-meters is the preordained failure. In some instances, between about 400 and about 600 cycles at a predetermined force of Newton-meters is the preordained failure. In some instances, between about 200 and about 400 cycles at a predetermined force of Newton-meters is the preordained failure. In some instances, between about 500 and about 1000 cycles at a predetermined force of Newton-meters is the preordained failure.

In certain implementations, preordained failure can be determined by the construction of one or more of the drive shaft 301, the sun gear 501 and at least one planet gear 120 of a material which is frangible or will otherwise fail after a predetermined number of cycles. The one or more of the drive shaft 301, the sun gear 501, and at least one planet gear 120 can be constructed as a component designed for embrittlement or weakening during a chosen sterilization process. In some implementations, the component can be embrittled or weakened via a gamma sterilization procedure that can be used to sterilize a fully assembled disposable tool or device prior to use. In certain implementations, the preordained failure can be determined by including a wt/wt % of one or more gamma-radiation-sensitive materials in the one or more components. Upon exposure to gamma radiation, gamma-radiation-sensitive materials undergo a reduction of one or more of tensile strength, impact resistance, hardness, compressive strength, tear strength, and flexural properties, such that the materials are embrittled due to the exposure. In some implementations, the one or more gamma-radiation-sensitive materials undergo embrittlement at an exposure less than about 200 kGy, 150 kGy, 100 kGy, 95 kGy, 90 kGy, 85 kGy, 80 kGy, 75 kGy, 70 kGy, 65 kGy, 60 kGy, 55 kGy, 50 kGy, 45 kGy, 40 kGy, 35 kGy, 30 kGy, 25 kGy, 20 kGy, 15 kGy, 10 kGy, or 5 kGy. In some implementations the one or more gamma-radiation-sensitive materials can be polytetrafluoroethylene (PTFE), fluorinated ethylene propylene (FEP), polyoxymethylene/polyacetals (Delrin, Celcon), aliphatic and amorphous grades of nylon polyamides, polymethylpentene, polypropylenes, or combinations thereof. In certain implementations, the one or more gamma-radiation-sensitive materials can be incorporated throughout one or more components as a wt/wt %/o of the gamma-radiation-sensitive material in all regions of the one or more components. In other implementations, the one or more gamma-radiation-sensitive materials can be incorporated in one or more components in a particular region of the one or more components, while the remaining regions of the one or more components are substantially free of any gamma-radiation-sensitive material, providing a desired wt/wt % for the one or more components when considered as a whole. In some implementations, the particular region of the one or more components having one or more gamma-radiation-sensitive materials can be one or more teeth of a gear. The wt/wt % of one or more gamma-radiation-sensitive materials in the one or more components can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Some implementations of shaft assembly 500 are formed from a drill connection shaft 301 that mates with a separate component sun gear 501. In some implementations, the sun gear 501 includes an opening 509 through a central axis, and the opening 509 can have a geometric profile that is complementary with a shaped portion 508 of the drill connection shaft 301. The corresponding geometric profiles provide a rigid connection that allows for the transmission of torque.

In some implementations of the shaft assembly 500, the assembly is formed as one integral component that includes the sun gear 501 and the drive shaft 301. Shaft assembly 500 can be formed by machining or by molding.

In some implementations, the entire output assembly 150 rotates relative to the housing 101. As shown in FIGS. 2-4 and 12-13, output assembly 150 can comprise an output shaft 152 and a plurality of planet gear carrier pins 151. The planet gear carrier pins 151 can be formed integrally with output shaft 152 or can be press-fit or fastened to the output shaft 152, provided that the axes of the planet gear carrier pins 151 are aligned parallel to each other and extend perpendicularly from the of the output shaft 152 from which they protrude. The proximal face 156 is disposed on the opposite end of the output assembly 150 from the distal end 155. The output shaft 152 and planet gear carrier pins 151 are rigidly connected such that any rotational torque forces placed on the planet gear carrier pins 151 are transferred to the output shaft 152.

In some implementations, one or more portions of the output assembly 150 rotate relative to the housing 101. As shown in FIGS. 5-9, output assembly 150 can comprise a retainer 170 and a planet carrier 180. Planet carrier 180 is formed with an axial opening having a proximal end 183 and distal end 184. In some implementations, the planet carrier 180 can include a plurality of mounting holes 181 configured to mount planet gear carrier pins 151 (not depicted in exploded views in FIGS. 8 and 9). In some implementations, the planet carrier 180 includes integral planet gear carrier pins 151. The proximal end 183 of the axial opening is configured to receive and mate with retaining feature 505 on the distal end of the shaft assembly 500. In some exemplary implementations, a protrusion or ridge within the proximal end 183 can mate with retaining feature 505 in a snap-fit engagement. The distal end 184 of the axial opening can be configured to mate with a workpiece or another workpiece-engaging component (not depicted herein), with connection features the same as the tip connection 160 described above. In some implementations, the distal end 184 of the axial opening of planet carrier 180 is configured to receive and mate with an output shaft insert 168, which contains a tip connection 160. In some exemplary implementations, retaining feature 505 engages with a portion of the output shaft insert 168 to connect the two components along their central axis but allow for relative rotation therebetween. The retainer 170 can be provided with an inner surface 171 which abuts against a surface 185 of the planet carrier 180. In some implementations a washer can be provided in between the surfaces 171/185 to reduce friction. The retainer 170 is mated with the housing 101 and connected via snap-fit, welding, threaded connection, or other methods of connection known in the art. The retainer 170 may have one or more voids 172 therein to reduce the material required to form the retainer 170 or to improve durability.

The housing 101 and output assembly 150 are configured to contain a plurality of planetary gears 120 within the internal volume between the housing 101 and the output assembly 150. The planetary gears 120 have gear teeth 121 and central axial openings 122 which are configured to mate with planet gear carrier pins 151. The planetary gears 120 are held in axial alignment by the engagement of the central axial openings 122 and the planet gear carrier pins 151, but can rotate freely around the planet gear carrier pins 151. The planetary gears 120 are disposed such that no two planetary gears 120 come into contact to prevent their rotation. The gear teeth of each planetary gear 120 engage with both the gear teeth 510 of the sun gear and a gear ring formed from an inward-facing plurality of gear teeth 104 which are disposed within the interior annular wall surface 103 of the housing 101. As the sun gear rotates and engages with the planetary gears, the planetary gears travel circularly around the central axis of the shaft assembly 500 due to their engagement with the gear teeth 104 of the gear ring in the housing 101, which is fixed to the body of the rotational tool. The circular travel of the planetary gears forces the rotation of the guide pins 151 and the corresponding rotation of the components of the output assembly 150 to which the guide pins 151 are attached or integrated within. In some implementations, such as the non-limiting exemplary implementations depicted in FIGS. 5-9, the rotation of the guide pins 151 causes rotation of a planet carrier 180 and output shaft insert 168. In some implementations, such as the non-limiting exemplary implementations depicted in FIGS. 2-4 and 12-13, the rotation of the guide pins 151 causes rotation of an output shaft 152.

The relative movement between components can be improved by making one or more of the housing 101, planet gears 120, drive shaft assembly 500, or output assembly 150 out of material that has a low coefficient of friction when in contact with another surface, coating the above components with a material that has a low coefficient of friction when in contact with another surface, applying a lubricant to the above components, positioning one or more low friction spacers 111/112 between adjacent components undergoing relative motion or rotation, or any combination of approaches in this list. One or more of the low-friction spacers may be constructed of a material or layers of material wherein after being exposed to a predetermined amount of friction and activity the material degrades or a layer is worn away exposing a layer which is easily degraded thereby adding debris to the planet gear and sun gear causing failure. In some implementations, a low friction spacer can be exposed to friction between planetary gear top 124 and housing 101, which leads to degradation of the spacer and failure of the overall system. In some implementations, a surface roughness or one or more protruding features can be provided on one or more portions of one or more surface components in order to impart a desired amount of degradation to a low friction spacer and introduce debris into the internal volume of the speed reduction assembly in order to induce failure after a predetermined amount of operation.

In some aspects, the integrated rotational speed reduction assembly 100 may be disposable. The integrated rotational speed reduction assembly 100 may be used for a predetermined number of uses. Alternatively, the integrated rotational speed reduction assembly 100 may be used for a predetermined duration of time. In some aspects, the integrated rotational speed reduction assembly 100 is intended for singular use. In further aspects, the reduction assembly is intended to be used for a predetermined number of rotations. In some aspects, the entire integrated rotational speed reduction assembly 100 is intended to be disposed of after a fixed usage period. In other aspects, portions of the integrated rotational speed reduction assembly 100 are intended to be disposed of while other portions are intended to be reused.

The drive shaft 301 may attach to a rotational tool that rotates the shaft during operation, such as a medical power tool 200. The integrated rotational speed reduction assembly 100 may accept various rotational inputs. In some aspects, it may accept inputs of up to about 1200 rpm in rotational speed. In other aspects, it may accept higher rotational speed inputs. In some aspects of the disclosure, it may accept inputs of at least about 150 rpm; in some aspects, it may accept inputs of at least about 450 rpm; in some aspects, it may accept inputs of at least about 1000 rpm; in some aspects, it may accept inputs of at least about 1250 rpm. In some aspects, it may accept inputs of up to about 1 N-m, up to about 2 N-m, up to about 3 N-m, up to about 4 N-m, up to about 5 N-m, up to about 6 N-m, up to about 7 N-m, up to about 8 N-m, up to about 9 N-m, or up to about 10 N-m.

The integrated rotational speed reduction assembly 100 can be used in methods of reducing rotational speed including connecting a rotational tool to an integrated rotational speed reduction assembly, such as one described herein, and then operating the rotational tool. The method may further include a step of disconnecting the rotational tool from the reduction assembly. The method may further include a step of disposing of the tool, the reduction assembly, or both after an acceptable number of uses or after an acceptable duration of use. The method may further include a step of connecting the reduction assembly to a second tool. The connection of the second tool may be made before connection of the first tool, after connection of the first tool, or while the first tool is connected. In some aspects, more tools may be connected in a variety of acceptable orders. The method may further include a step of connecting a torque limiting device to the integrated rotational speed reduction assembly.

The integrated rotational speed reduction assemblies described herein can provide for predetermined rotational speed reduction ratios. The rotational speed reduction ratio is determined by the relative number of gear teeth provided on the sun gear 501, planetary gears 120, and the gear ring formed of gear teeth 104 in the housing 101, and the relative sizes of the gears. The gearing ratio can be predetermined as the ratio of (number of sun gear teeth 510 plus the number of gear ring teeth 104)/(number of sun gear teeth 510). The gearing ratio represents the reduction in rotational speed, such that, for example, a value of 5:1 indicates that an input speed of 1000 rpm would create an output speed of 200 rpm. In some implementations, the gearing ratio can be provided as about 2.5:1, about 3:1, about 3.5:1, about 4:1, about 4.5:1, about 5:1, about 5.5:1, about 6:1, about 7:1, about 8:1, about 9:1, about 10:1, or about 11:1. Input torque is increased by the gearing ratio to produce a correspondingly higher output torque (before efficiency losses).

The speed reduction reduces the RPMs which are applied to the integrated torque-limiting device. Some suitable torque-limiting devices that may be used with the integrated rotational speed reduction assemblies herein are described in International Patent Application No. PCT/US16/35712, filed Jun. 3, 2016. International Patent Application No. PCT/US16/55798, filed Oct. 6, 2016, U.S. patent application Ser.

No. 15/691,595, filed Aug. 30, 2017, and U.S. patent application Ser. No. 15/583,803, filed May 1, 2017, which are incorporated herein in their entireties for all purposes. The gearless torque-limiting device disclosed herein is disposable and not suitable for re-sterilization and reuse beyond the single intended usage. Too great an RPM applied to a disposable plastic torque-limiting pair of corresponding undulations can heat-up and otherwise damage the torque-limiting device prematurely causing it to fall out of specification.

Aspects of the undulated torque limiting assembly 600 are a generally cylindrical shape with a cup shaped drive cap 12 with connector mount or other structure to facilitate use with a motorized device. For example, formed on or as part of the output assembly's distal end 155 are drive teeth 158 which mate with the generally hollow cylindrical body 614. The drive teeth are mated to the cylindrical body 614 at its proximal end 615. The distal end 155 may be snap-fitted to cylindrical body 614, or may be welded, adhered, or attached by any equivalent thereof.

The hollow cylindrical body 614 has an open distal end 616 with a circumferential rim 617 on the exterior therein proving a seat and guide for a tool collar 620. A lower shank 700 is fit inside the body 614. The lower shank is generally cylindrical of a size to allow to rotate axially within the body. Opposite the circumferential rim on the interior 618 of the cylindrical body 614 is an upper shank component 200 formed as part of the cylindrical hollow body 614 with at least an axial bore 810 and an upper or second torque-limiting interface 850 disposed on the inside of the cylindrical body 614.

The tool collar is formed of plastic and is a guide for a shaft. The tool collar 620 has a flange 622 extending radially of a size and shape to fit rotatably into the circumferential rim 617. The tool collar has a roughly square leg 625 extending on one side of the flange 622 and a nose 627 extending on the opposite of the flange. A shaped channel 629 passes through the tool collar thereby forming a fluid connection for inserting tools. Tools may be removable. Tools include, but are not limited to cutting blades or resectors, fastener fixing ends such as shaped tips and sockets.

Figure 14A:
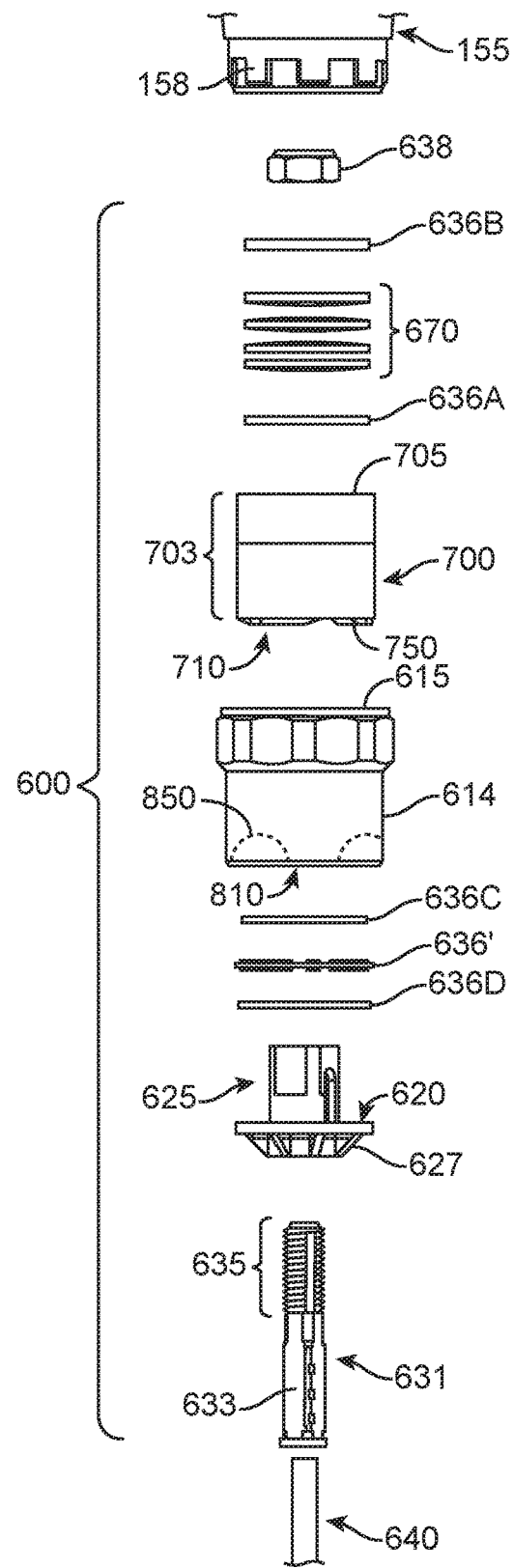
FIG. 14A is an assembly view of aspects of a rotational speed reduction with integral gearless torque limiting.
Figure 14B:
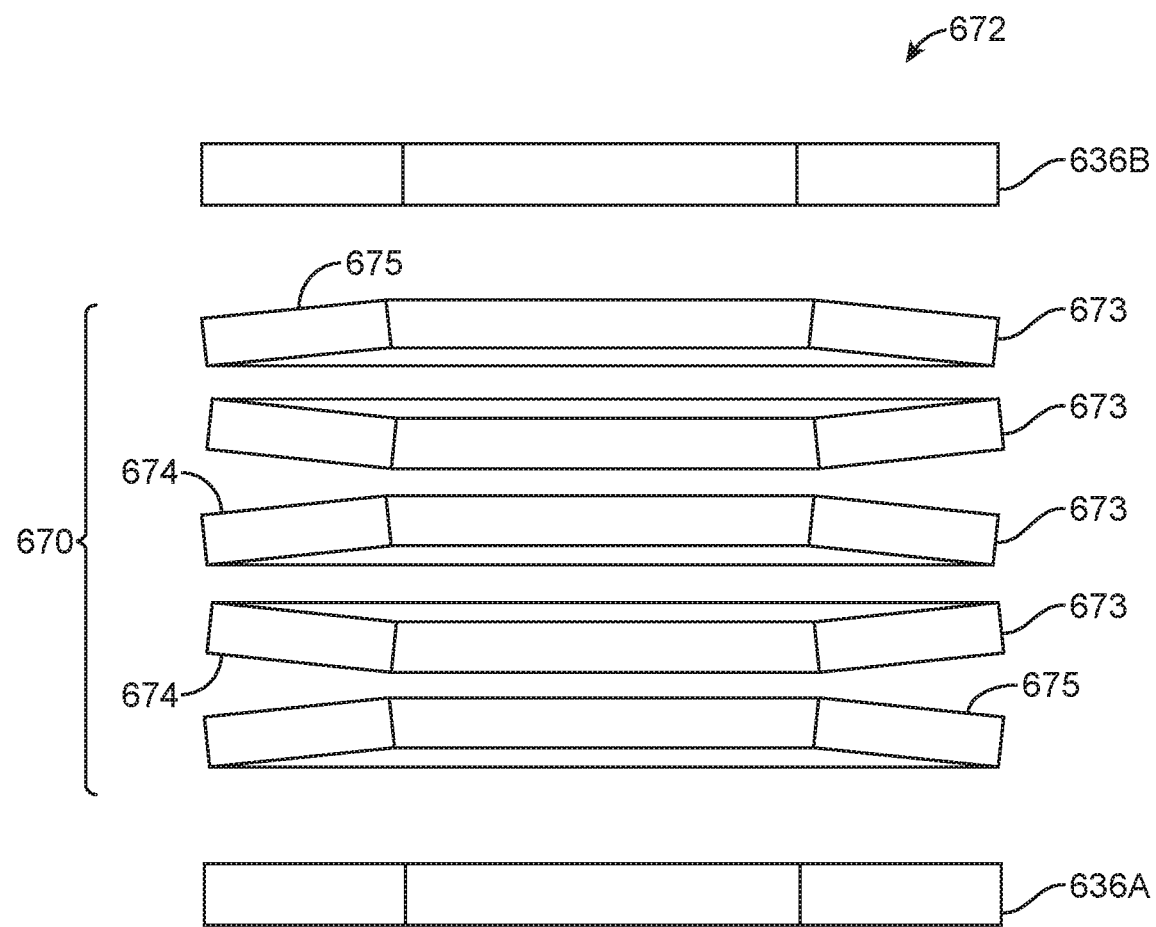
FIG. 14B is a view of aspects of a MBWA of a rotational speed reduction with integral gearless torque limiting.
Figure 15:
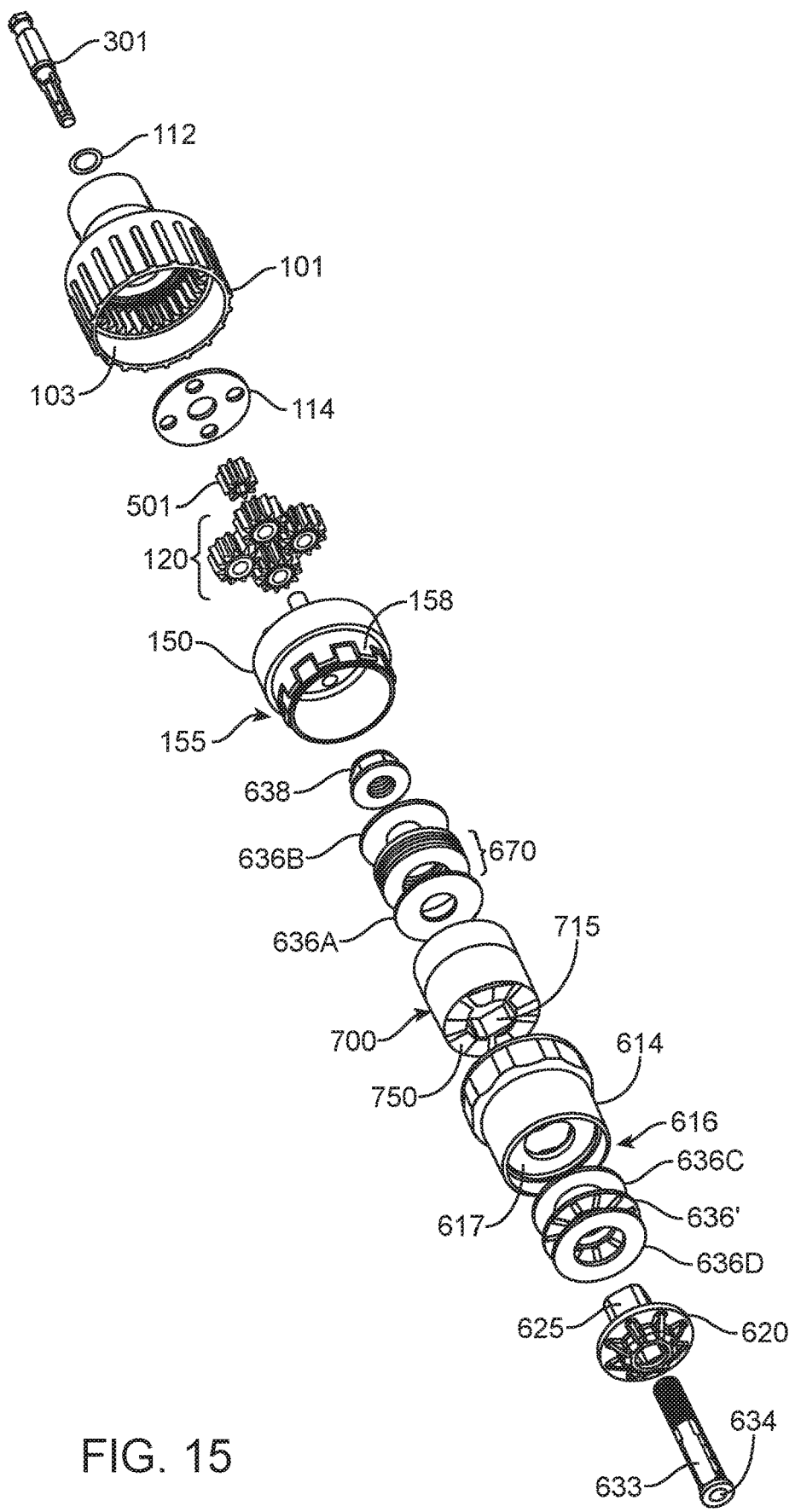
FIGS. 15-16 are assembly views of aspects of an integrated rotational speed reduction with integral gearless torque limiting.
Figure 16:
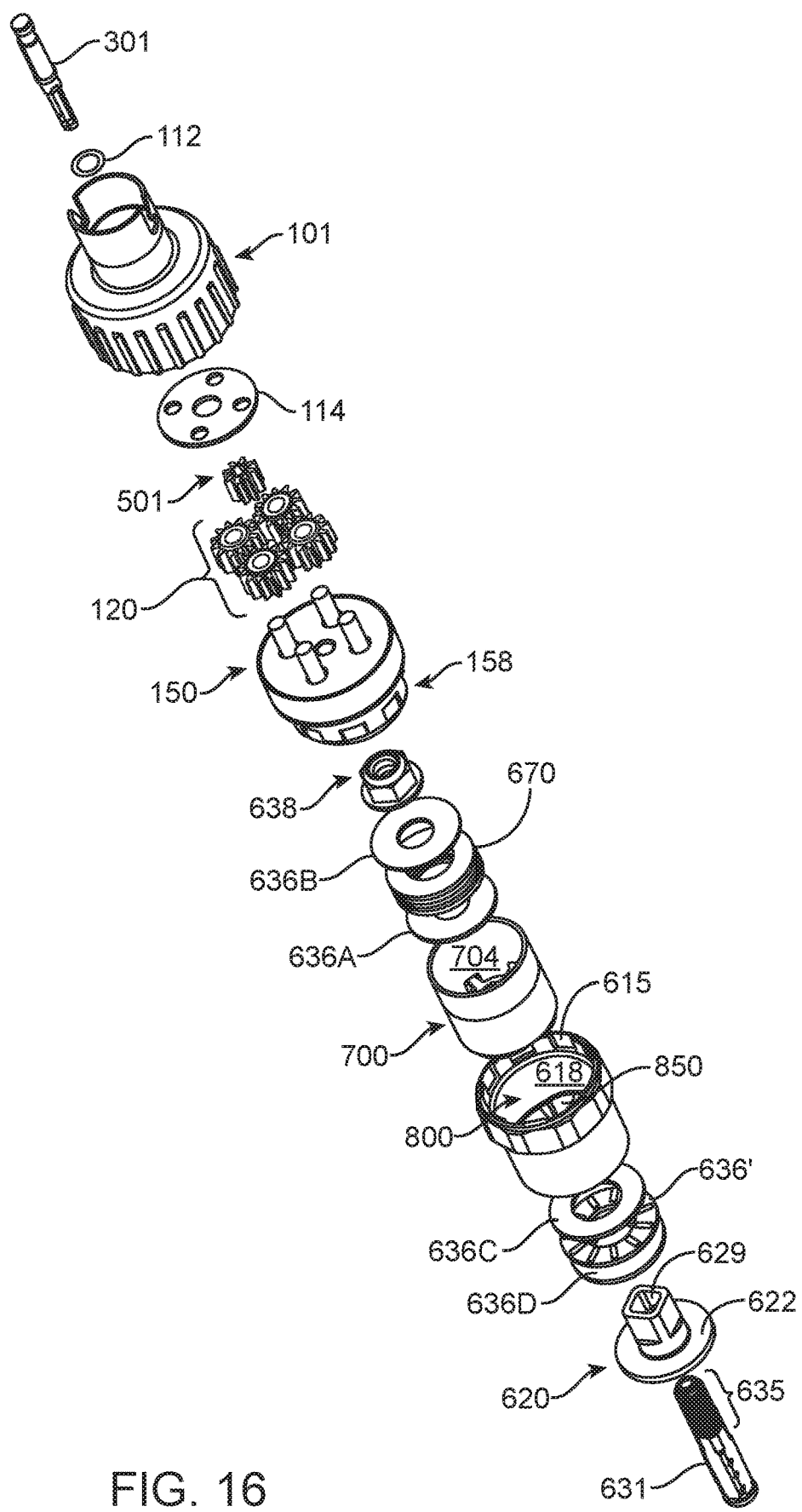

During assembly the lower shank component 700 fits movably within the hollow body 614. The lower shank has a drive shaft 710 therethrough. On one side of the lower shank there is a lower or first torque-limiting interface 750 and the other side of the lower shank 700 may include a retaining cavity 703 configured to retain biasing elements, such as a grouping of belleville washers, also known as a coned-disc spring, hereinafter referred to as Multiple Belleville Washer Assembly ("MBWA") 670 with a fluid passage 672 through the center of member (FIG. 14B). Each washer member 673 has a base 674 and a cone 75 and they are set in pairs alternating with base 674 to base 674 and cone 675 to cone 675 with a fluid passage 672 therethrough. In some implementations, the MBWA is replaced by a compressible material with durometer ratings between about 50 durometer and 100 durometer, within an annular wall 704.

A tool shaft 631 fits firmly into the tool collar channel 629. The tool shaft may be partially hollow with an open front end 634. One or more catches 633 are formed on a portion of the tool shaft whereby the catches mate with the channel 629 and the tool shaft is restricted from rotation within the channel. The catches are depicted as one or more flat sides. The tool channel 634 extends axially, at least partially, in the tool shaft from the front end 631 of the tool shaft. A series of threads 635 are formed on a back portion of the tool shaft.

Optionally a first washer 636 is interposed between the flange and circumferential rim 617. The washer is formed of plastic and has high lubricity. In some instances, depending on design requirements and use a flat roller bearing washer 636' between a first washer 636C and a second washer 636D may be used with or in place of the washer 636. At higher speed the roller bearing washer reduces frictional forces at the circumferential rim 617. Aspects of the method of in-line torque application at predetermined forces include reducing or eliminating melting of the circumferential rim during the life time of the device.

The lower shank 700 is inserted into the body 614 through the proximal end 615 and the lower torque-limiting interface 750 sits on the upper torque-limiting interface 850 and the two interfaces together form a torque limiting engagement. The lower shank is generally cylindrical of a size to allow to rotate axially within the body. The square leg and tool shaft extends through the axial bore 810 and the drive shaft 710. Formed as part of the drive shaft 710 are a series of drive catches 715 which mate with the square legs 625 whereby when the lower shank 700 rotates the square leg rotates as does any tools and the affixed therein.

A threaded retaining member 638 such as a nut or other fixture fits onto the threads 635 of the tool shaft and is used to compress the MBWA 670 against the lower shank and hold the components inside the device inline. This engagement provides a locking mechanism for tool shaft 632 relative to the body 614 via lower shank 700 when pressure is applied across lower shank 700 and upper shank 800. A preselected force is applied across lower shank 700 and upper shank 800 via the biasing element MBWA 670 within cylindrical body 614.

In operation drill connection shaft 301 is connected to a rotating force. A workpiece engaging tip 640 is connected to a workpiece, fastener, or other fixture that requires rotation for application. The application of a rotational force to the device causes the first torque-limiting interface 750 and the second torque-limiting interface 750 (collectively referred to as the torque limiter) support on the shanks to engage and rotate the tool until such time as the amount of force necessary to rotate the tool further is exceeded by the force the tool is experiencing during operation. At that point the torque-limiter disengages and one of the first and second torque-limiting interfaces moves over the other as opposed to with each other. When rotating a torque limiting assembly within a plastic body with an attachment at the circumferential rim the plastic body will tend to melt if sufficient frictional forces are applied.

The hollow cylindrical body 614 has an open distal end 616 with a circumferential rim 617 on the exterior therein proving a seat and guide for a tool collar 620. The lower shank 700 is fit inside the body 614. Opposite the circumferential rim on the interior 618 of the cylindrical body 614 is an upper shank component 800 formed as part of the cylindrical hollow body 614 with at least an axial bore 810 and a torque-limiting interface 850 disposed on the inside of the cylindrical body 614.

The lower shank 700 is once inserted into the body 614 through the proximal end 615 and the lower torque-limiting interface 750 sits on the upper torque-limiting interface 850. The square leg and tool shaft extends through the axial bore 810 and the drive shaft 710. Formed as part of the drive shaft 710 are a series of drive catches 715 which mate with the square legs 625 whereby when the lower shank 700 rotates the square leg rotates as does any tools 640 affixed within the shaped channel 629.

Figure 17:
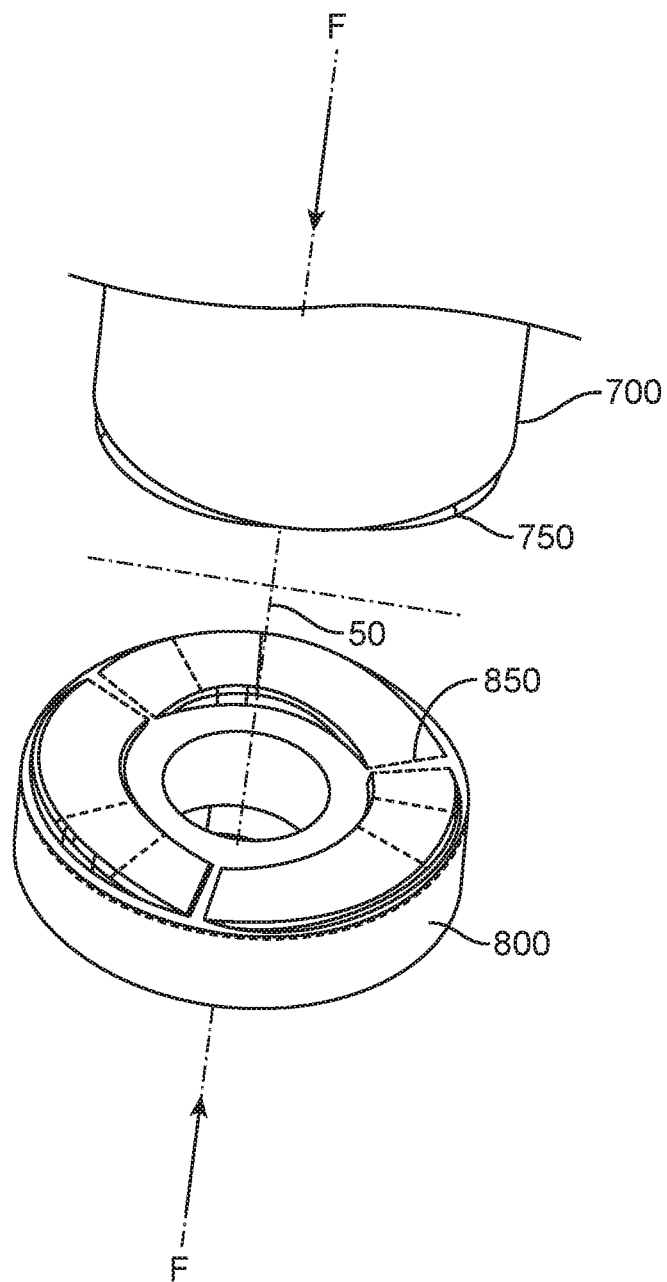
FIG. 17 shows an exploded assembly perspective view of some aspects of torque-limiting mechanisms of the present disclosure.
Figure 18:
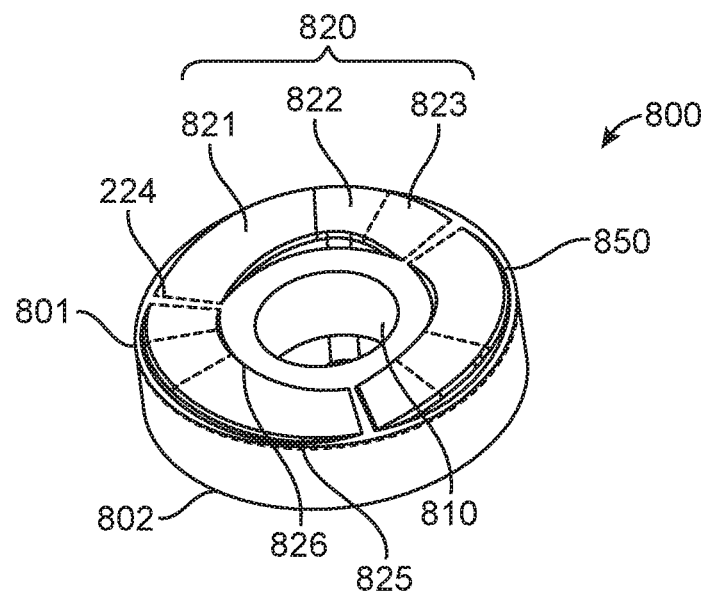
FIG. 18 shows a perspective view of some aspects of components of torque-limiting mechanisms of the present disclosure.
Figure 19:
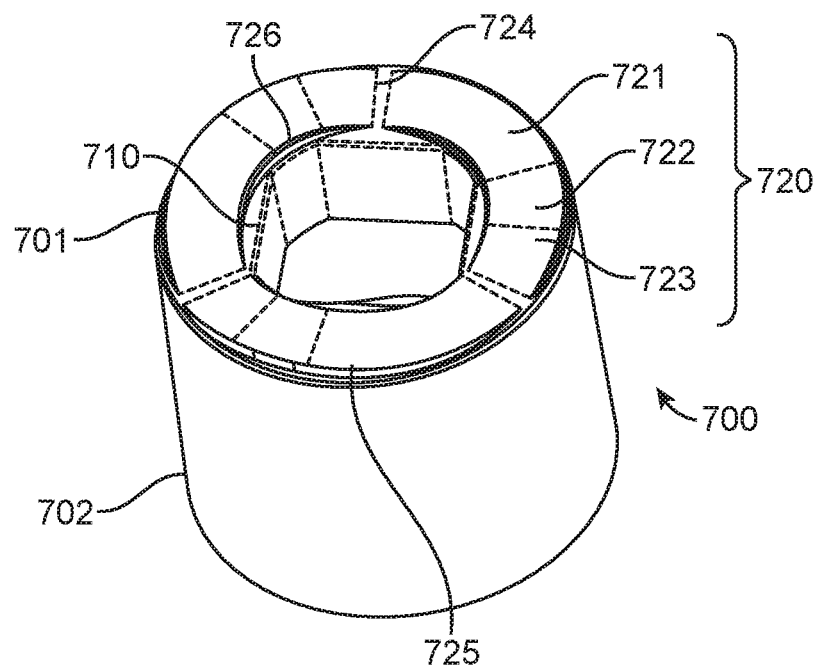
FIG. 19 shows a perspective view of some aspects of components of torque-limiting mechanisms of the present disclosure.

FIGS. 17, 18 and 19 shows some aspects of some implementations of torque-limiting mechanisms of the present disclosure. The torque-limiting mechanisms has an upper shank component 800, a lower shank component 700, and a biasing element biasing element MBWA 670 (shown 14A-16) configured to apply a force (F) along an axis 50. Upper shank component 800 can have a proximal end 801, a distal end 802, an axial bore 810 connecting the proximal end and the distal end, and a torque-limiting interface 850 disposed on the proximal end. Lower shank component 700 can have a proximal end 701, a distal end 702, a drive socket 710 connecting the proximal end and the distal end, and a torque-limiting interface 750 disposed on the proximal end. The upper shank component and the lower shank component are aligned along an axis 50 in the direction of the axial bore 810 and the drive socket 710 with the torque-limiting interface 850 in contact with the torque-limiting interface 750. The biasing element 670 is configured to apply a compressive force (F) along the axis to compress the torque-limiting interface against the torque-limiting interface. The upper shank component 800 and the lower shank component 700 are configured to engage to rotate together when torque is applied to the lower shank component via the drive socket and are configured to disengage when a predetermined torque limit is exceeded. When disengaged, the torque-limiting interfaces 750/850 slide past each other in relative rotation about the axis 50. Drive socket 710 can have any suitable shape that allows for the transmission of torque to the lower shank component 700. Suitable shapes for the drive socket 710 include geometric shape profiles such as hexagons, squares, or truncated/rounded versions thereof. Those of ordinary skill in the art can appreciate that the torque-limiting mechanisms of the present disclosure can be incorporated into any systems or devices that require torque-limited rotation between subcomponents of those systems or devices. In some implementations, the torque-limiting mechanisms of the present disclosure can be incorporated into torque-limited drivers for use in surgical applications; such drivers can be hand-driven or driven with power tools at higher rates of rotation. Those of ordinary skill in the art can appreciate that the torque-limiting mechanisms of the present disclosure can be incorporated into any systems or devices that require torque-limited rotation between subcomponents of those systems or devices. In some implementations, the torque-limiting mechanisms of the present disclosure can be incorporated into torque-limited drivers for use in surgical applications; such drivers can be hand-driven or driven with power tools at higher rates of rotation.

FIGS. 18 and 19 show further aspects of some implementations. Upper shank component 800 can have a torque-limiting interface 850 with a plurality of undulations 820 arranged around the axial bore and separated by a plurality of transition regions 824. The lower shank component 700 can shave a torque-limiting interface 750 having a plurality of undulations 720 arranged around the drive socket and separated by a plurality of transition regions 724, the first and second pluralities being equal in number. Each undulation 720/820 can be formed as an upslope 721/821, a peak 722/822, and a downslope 723/823.

In some implementations, the torque-limiting interfaces 750/850 do not contain any step or drop-off greater than about 0.005". One or more cutouts or slots (not shown) can be provided in one or more of the upslopes, 721/721, peaks 722/822, or downslopes 723/823 to collect at least a portion of any debris generated during operation. In some embodiments, downslope 723/823 is designed with maximum length to provide the softest downward angle back down to the initial height of the next upslope 721/821. During powered rotation, a softer downslope mitigates degradation of the downslope 723/823 material. Such degradation adversely impact performance as the torque-limit at which disengagement occurs can change as the material degrades.

Each undulation 720/820 sweeps through a portion of the 360 degrees around the central axial bore 810 or drive socket 710, with the plurality of undulations 720/820 covering a total portion of the 360 degrees around the central axial bore. In some implementations, the total portion covered by the plurality of undulations 720/820 can be at least about 65% of the 360 degrees (about 235 degrees), at least about 70% of the 360 degrees (about 255 degrees), at least about 80% of the 360 degrees (about 285 degrees), at least about 83% of the 360 degrees (about 300 degrees), at least about 90% of the 360 degrees (about 324 degrees), at least about 95% of the 360 degrees (about 345 degrees), or at least about 98% of the 360 degrees (about 350 degrees). The portion not covered by the plurality of undulations 720/820 is filled with transition regions 724/824 between the end of each downslope 723/823 and the beginning of the next upslope 721/821. Each transition region 724/824 can be selected to be no greater than about 35 degrees, no greater than about 20 degrees, no greater than about 15 degrees, no greater than about 10 degrees, no greater than about 5 degrees, no greater than about 4 degrees, no greater than about 3 degrees, no greater than about 2 degrees, no greater than about 1 degree, or can be eliminated entirely if the end of each downslope 723/823 is immediately adjacent to the beginning of the next upslope 721/821.

A softer downslope angle the torque-limiting interfaces 750/850 can substantially mitigate or eliminate any "click" or audible indication that the upper shank component 800 and lower shank component 700 have slipped past each other during a disengagement, also referred to herein as an actuation, when the predetermined torque limit has been exceeded. In some implementations, an actuation indicating system can be incorporated in the overall torque-limiting driver to create one or more "clicks" when the upper shank component 800 and lower shank component 700 have slipped past each other. In some implementations, the actuation indicating system can include a flag feature on either lower shank component 700 or upper shank component 800 that impacts one or more spokes, protrusions, or other physical features on another component in the system as relative rotation occurs.

Upper shank component 800 and lower shank component 700 can be formed from various materials. Suitable materials include stainless steels, aluminums, plastic materials, or composites including plastic. Plastic and other economical equivalents improve cost efficiency of production while providing high tensile strength, resistance to deformation, etc. Effective materials include plastics, resins, polymers, imides, fluoropolymers, thermoplastic polymers, thermosetting plastics, and the like as well as blends or mixtures thereof. In some implementations, 30% glass-filled polyetherimide can be used to form one or more of the above components. For components formed from stainless steels or aluminums, the shank components can be heat treated, passivated, or anodized via suitable methods known to those of ordinary skill in the art. In some implementations, aluminum shank components can be finished with a hard anodize finish per MIL-A-8625F, type III, class 2. In some implementations, stainless steel 440c shank components can be heat treated per AMS 2759/5D to 58Rc and passivated with treatment with nitric acid and/or sodium dichromate. Other heat treatments and passivation methods known in the art are also suitable. In some implementations, corresponding pairs of gear rings are formed from different materials. In some preferred implementations, one shank component 100/200 is formed from stainless steel or aluminum and the corresponding gear ring is formed from 30% glass-filled polyetherimide (PEI) resin. In some implementations the shank components 700/800 can be made from the same material.

According to aspects of one or more exemplary implementations, components of the torque-limiting mechanisms of the present disclosure are resistant to sterilization, cleaning, and preparation operations. For example, the upper shank component and lower shank component may be configured to withstand sterilization by methods including radiation (e.g., gamma rays, electron beam processing), steam (e.g., autoclave), detergents, chemical (e.g., Ethylene Oxide), heat, pressure, inter alia. For example, materials may be selected according to resistance to one or more selected sterilization techniques.

The material selection and surface treatments applied to the torque-limiting interfaces 750/850 can affect the predetermined torque limit. The static friction between the torque-limiting interfaces 750/850 determines when disengagement will occur, as the rotation force can overcome the static friction holding the interfaces into engagement with each other. Greater contact surface area of the opposing interfaces, via wider undulations 720/820 or other aspects of the shape/profile of the undulations 720/820, will increase the resistance to actuation and lead to a higher predetermined torque limit.

In some preferred implementations, upper shank component 800 and lower shank component 800 are both mad from 30% glass-filled polyetherimide (PEI) resin. In some implementations, a glass-filled ULTEM® PEI from Saudi Basic Industries Corporation (SABIC) can be used to form the upper shank component 800 and lower shank component 700 via machining or molding. In some implementations, a lubricant is disposed on one or both of torque-limiting interfaces 750/850. Such lubricants are useful to avoid excessive heat build-up during actuations at high rates of rotation, which can melt or degrade the PEI material.

Figure 20A:
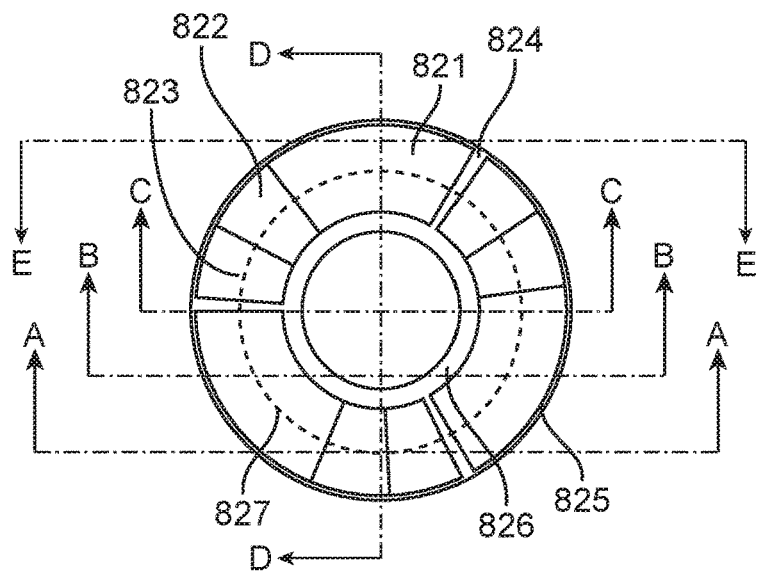
FIG. 20A shows a top view of some aspects of components of torque-limiting mechanisms of the present disclosure.
Figure 20B:
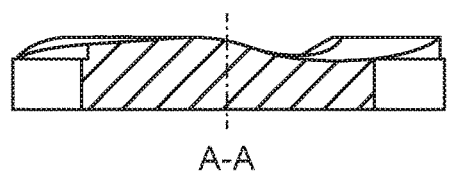
FIGS. 20B-20F show cut-away sectional views along the sections marked A-A, B-B, C-C, D-D, and E-E in FIG. 20A.
Figure 20C:
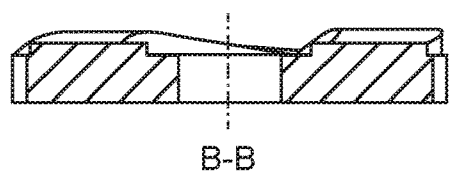
Figure 20D:
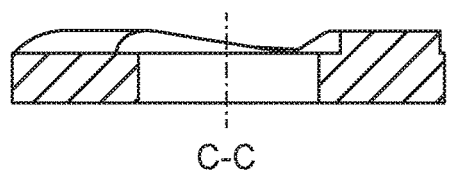
Figure 20E:
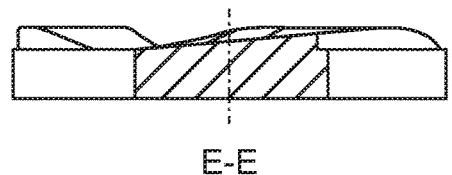
Figure 20F:
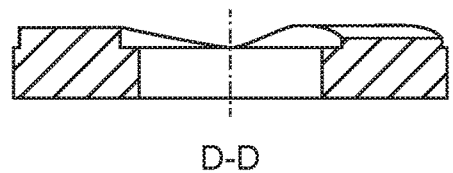

The shape of some implementations of undulations 720/820 can be seen in FIGS. 20A-20F. FIG. 20A shows a top view of the torque-limiting interface 750 at the proximal end 801 of upper shank component 800. FIG. 20B shows a cut-away view of the upper shank component 800 along line A-A shown in FIG. 20A. FIG. 20C shows a cut-away view of the upper shank component 800 along line B-B shown in FIG. 20A. FIG. 20D shows a cut-away view of the upper shank component 800 along line C-C shown in FIG. 20A. FIG. 20E shows a cut-away view of the upper shank component 800 along line E-E shown in FIG. 20A. FIG. 20F shows a cut-away view of the upper shank component 800 along line D-D shown in FIG. 20A. The number of undulations 720/820 is determined by the size of the upper shank component 800 and lower shank component 700 and the shape of the undulations 720/820. The size of the shank components 700/800 determines the functional path length that the plurality of undulations may have. The functional path length refers to the circumferential length of a circular path along the midpoint of the undulations, shown as a dashed circle 827 in FIG. 20A. A larger diameter shank component allows for a larger functional path length. The shape of the undulations 720/820 refers to the inclination angle of the upslope 721/821, the length of the peak 722/822, and the declination angle of the downslope 723/823. Sharper inclination and declination angles and shorter peak lengths can lead to a shorter functional path length for each individual undulation, which would allow for more undulations to be placed onto the torque-limiting interfaces 750/850. The torque-limiting interfaces may have two undulations, three undulations, four undulations, or five or more undulations. Three or more undulations are used in some preferred implementations, as systems with only two undulations may be less stable during actuations at higher rates of rotation.

The width of the undulations can span the entirety of the annular ring of the proximal ends of the upper shank component and lower shank component between the drive socket 710 or axial bore 810 and outer edges of those components, or can be reduced widths to accommodate adjoining parts to avoid undesired contact points or friction. The width must be sufficient to provide adequate interface contact area with the opposing set of waves to create the friction necessary for torque transmission. Larger widths allow for the applied force to be distributed over larger surface areas and reduce stress on the components.

The inclination angle of each upslope 721/821 can be about 3 to about 15 degrees, more preferably about 5 to about 9 degrees, more preferably about 6 to about 8 degrees, and most preferably about 7 degrees. The inclination angle is measured along the functional path length along the midpoint of the undulations, as the angle along the interior edge 726/826 will be higher due to the shorter path length, and the angle along the exterior edge 725/825 will be lower due to the longer path length. The declination angle of each downslope 723/823 can be about 5 to about 45 degrees, more preferably about 10 to about 30 degrees, more preferably about 10 to about 20 degrees, and most preferably about 15 degrees. The declination angle is measured along the functional path length along the midpoint of the undulations. In some preferred implementations, the ratio of the functional path length of the upslope 721/821 of each undulation to the functional path length of the downslope of each undulation can be about 3.0:1, about 2.5:1, about 2.4:1, about 2.3:1, about 2.2:1, about 2.1:1, about 2.0:1, about 1.9:1, about 1.8:1, about 1.7:1, about 1.6:1, about 1.5:1, about 1.4:1, about 1.3:1, about 1.2:1, about 1.1:1, or about 1.0:1. In some preferred implementations the ratio can be between about 2.2:1 and about 1.8:1, or more preferably about 2.0:1.

Each peak 722/822 has an even height across its surface from the interior edge 726/826 to the exterior edge 725/825 at each radial line from the central axis of the respective shank component 100/200. In some implementations the functional path length of each peak 722/822 is approximately equal to the length of each of the transition regions 724/824, such that the peaks 722/822 of each torque-limiting interface are complementary and mate with the transition regions 724/824 of the opposing torque-limiting interface.

Figure 21A:
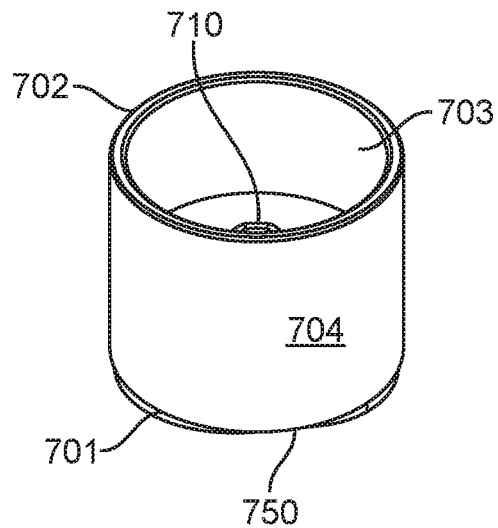
FIGS. 21A and 21B show perspective views of some aspects of components of torque-limiting mechanisms of the present disclosure.
Figure 21B:
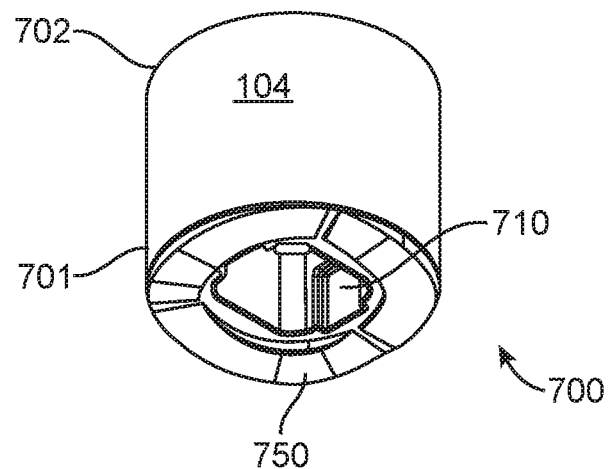
Figure 21C:
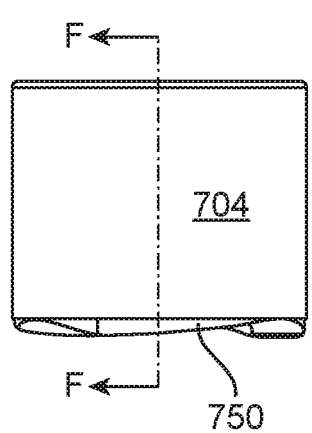
FIG. 21C shows a side view of some aspects of components of torque-limiting mechanisms of the present disclosure; and, FIG. 21D shows a cut-away section view along the section marked F-F in FIG. 21C.
Figure 21D:
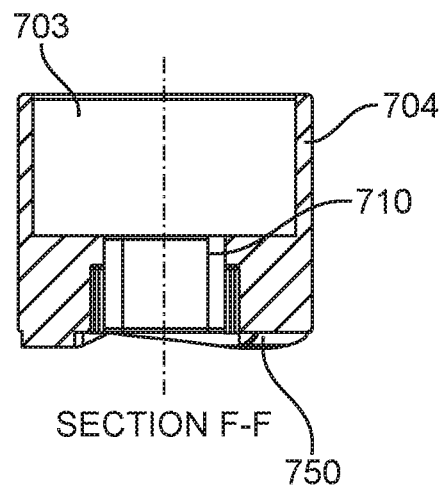

FIGS. 21A-21D show some aspects of an implementation of a lower shank component 700 the present disclosure. FIG. 21A and FIG. 21B show perspective views of an implementation of a lower shank component 700. FIG. 21C shows a side view while FIG. 21D shows a cross-sectional view along the line D-D shown in FIG. 21C. The lower shank component 100 can include a retaining cavity 703 configured to retain biasing element within a wall 704 located at the distal end 702. The retaining cavity 703 provides for a volume in which a biasing element can be compressed, so that if biasing element expands radially during compression it will be retained within retaining cavity 703 rather than impinging or contacting other components within the system.

Biasing element provides compressive force between the upper shank component and lower shank component to place the torque-limiting interfaces 750/850 into frictional contact with each other. Other suitable biasing elements can include springs, grommets or washers of compressible materials such as rubber. In some implementations, compressible materials with durometer ratings between about 50 durometer and 100 durometer can be used as biasing elements. The biasing element can be compressed by other components in a torque-limiting driver. The amount of compression applied to a biasing element can be used to set the predetermined torque limit at which disengagement/actuation of the torque-limiting mechanism occurs. Higher compressive forces created by the biasing element will create higher predetermined torque limits.

According to aspects of one or more exemplary implementations, the torque-limiting mechanisms of the present disclosure are capable of imparting torques of up to about 6 N-m at various rotational speeds. For example, the torque output range may be selected between about 0.5 N-m and about 6 N-m and utilized in combination with a rotational speed selected between about 150 RPMs and about 1300 RPMs. Typically, the torque requirement is different for different operations and for different implants. For example, applications may include those in the field of orthopedic surgery, construction and emplacement of implants, etc. In such instances, the predetermined torque limit may be about 6 N-m, depending on an implant's specifications. Smaller fasteners may utilize lower torque limits between about 0.1 N-m and about 2.0 N-m. In some instances the torque-limiting mechanisms of the present disclosure will provide a predetermined torque of at least one of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 Newton-meters (N-m) of torque at a rotational speed of at least one of 50, 100, 150, 200, 250, 300, 350, 400, 450, 500, 550, 600, 650, 700, 750, 800, 850, 900, 950, 1000, 1050, 1100, 1150, 1200, 1250, or 1300 RPMs over at least one of 5, 10, 20, 30, 40, 50, 60, 70, 80, 90, 100, 105, 110, 120, 150, 180, 200, 220, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 actuations while remaining within a specified operational range.

While the method and apparatus have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

In this regard it should be understood that for practical reasons and so as to avoid adding potentially hundreds of claims, the applicant has presented claims with initial dependencies only.

Support should be understood to exist to the degree required under new matter laws-including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Such terms should be interpreted in their most expansive forms so as to afford the applicant the broadest coverage legally permissible.

What is claimed:

1. A single use in-line speed reduction torque-limiting assembly comprising:
    a shaft assembly comprising a drive shaft and a sun gear attached to said drive shaft;
    a housing;
    a plurality of planetary gears each having a plurality of gear teeth;
    an output assembly; and, an undulated torque-limiting assembly with a shaped channel for receiving a tool;

wherein one or more of said plurality of planetary gears and said plurality of gear teeth on each said planetary gear are non-metal; and, wherein said one or more of said non-metal teeth are frangible after a predetermined number of use cycles of said non-metal teeth.

2. The single use in-line speed reduction torque-limiting assembly of claim 1 wherein said undulated torque-limiting assembly comprises:

an upper shank component with a first torque-limiting interface disposed on said upper shank component's proximal end;

a lower shank component with a second torque-limiting interface disposed on said lower shank component's proximal end;

a drive socket connecting said upper shank component with said lower shank component;

a biasing element configured to apply compressive force (F) along an axis that runs parallel to the sides of said channel to compress said first torque-limiting interface against said second torque-limiting interface;

wherein said upper shank component and said lower shank component are aligned along said axis with said first torque-limiting interface in contact with said second torque-limiting interface;

wherein said upper shank component and said lower shank component are configured to engage to rotate together when torque is applied to a drive socket connected to said lower shank component; and, wherein said upper shank component and said lower shank component are configured to disengage when a predetermined torque limit is exceeded.

3. The single use in-line speed reduction torque-limiting assembly of claim 1, wherein:

said single use in-line speed reduction torque limiting assembly is configured to receive a rotational input to said shaft assembly of up to about 150 rpm, about 250 rpm, about 500 rpm, about 750 rpm, about 1000 rpm, about 1250 rpm, about 1500 rpm, or about 2000 rpm;

said single use in-line speed reduction torque limiting assembly is configured to provide a gearing; ratio such that the rotational speed is reduced between said input to said shaft assembly and an output to the of said output assembly by said gearing ratio and a torque is increased between said rotational input to said shaft assembly and said output of said output assembly by said gearing ratio; and the gearing ratio is provided as about 2.5:1, about 3:1, about 3.5:1, about 4:1, about 4.5:1, about 5:1, about 5.5:1, about 6:1, about 7:1, about 8:1, about 9:1, about 10:1, or about 11:1.

4. The single use in-line speed reduction torque-limiting assembly of claim 1, wherein:

said output assembly comprises an output shaft having a plurality of guide pins, with each guide pin mating with one of said plurality of planetary gears;

said housing comprises a gear ring of a plurality of gear teeth disposed on an interior surface of said housing, with said gear ring configured to engage with said gear teeth of said planetary gears;

said output shaft is configured to rotate in response to rotation of said shaft assembly, via engagement between said sun gear and said planetary gears and engagement between said planetary gears and said gear ring.

5. The single use in-line speed reduction torque-limiting assembly of claim wherein:

said first torque-limiting interface comprises a first plurality of undulations arranged around an axial bore and separated by a first plurality of transition regions;

said second torque-limiting interface comprises a second plurality of undulations arranged around a drive socket and separated by a second plurality of transition regions, the first and second pluralities being equal in number; and each undulation comprises an upslope, a peak, and a downslope.

6. The assembly of claim 5 wherein:

each upslope has an inclination angle between about 3 degrees and about 15 degrees.

7. The assembly of claim 5 wherein each upslope has an inclination angle between about 5 degrees and about 9 degrees.

8. The assembly of claim 5 wherein:

each upslope has an inclination angle between about 6 degrees and about 8 degrees.

9. The assembly of claim 5 wherein:

each upslope has an inclination angle of about 7 degrees.

10. The assembly of claim 5 wherein said predetermined torque limit is between about 0.1 Newton-meter and 3.0 Newton-meters.

11. The assembly of claim 5 wherein said predetermined torque limit is between about 3.0 Newton-meter and 6.0 Newton-meters.

12. The assembly of claim 2 wherein the first torque-limiting interface and second torque-limiting interface each comprise three undulations.

13. The assembly of claim 2 wherein the first torque-limiting interface and second torque-limiting interface each comprise four undulations.

14. The assembly of claim 2 wherein said first torque-limiting interface and second torque-limiting interface each comprise five undulations.

15. The assembly of claim 2 wherein said single use in-line speed torque limiting assembly provides a predetermined torque between about 0.1 Newton-meter and about 6 Newton-meters of torque at a rotational speed between about 50 RPM and about 1300 RPM over at least one of 5, 10, 20, 30, 40, 50, 60, 70, 80, 90, 100, 105, 110, 120, 150, 180, 200, 220, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, or 2500 actuations while remaining within a specified operational range.

16. A method for reducing rotational speed and torque-limiting of one or more disposable rotational tools, the method comprising:

forming an input by connecting a drive shaft of the single use in-line speed reduction torque-limiting assembly of any of claims 1-5 to a first rotational tool;

operating said first rotational tool; and, whereby said single use in-line speed reduction and torque-limiting assembly provides a reduced speed and torque-limited output.

17. The method of claim 16, wherein a ratio of speed input to output is between about 3:1 and about 5:1.

18. The method of claim 16, wherein said single use in-line speed reduction and torque-limiting assembly increases torque applied to said input to a higher torque output.

19. The method of claim 18, wherein a ratio of torque input to torque output is between about 1:3 and about 1:5.

20. The single use in-line speed reduction torque-limiting assembly of claim 1, wherein at least one of the frangible teeth will fail after a predetermined number of use cycles.

21. The single use speed reduction torque-limiting assembly of claim 1, wherein the one or more non-metal gears comprise one or more gamma-radiation-sensitive materials in at least a region.

22. The single use in-line speed reduction torque-limiting assembly of claim 21, wherein said or more gamma-radiation-sensitive materials undergo embrittlement at an exposure of one of less than 200 kGy, 50 kGy, 100 kGy, 95 kGy, 90 kGy, 85 kGy, 80 kGy, 75 kGy, 70 kGy, 65 kGy, 60 kGy, 55 kGy, 50 kGy, 45 kGy, 40 kGy, 35 kGy, 30 kGy, 25 kGy, 20 kGy, 15 kGy, 10 kGy, and 5 kGy.

23. The single use in-line speed reduction torque-limiting assembly of claim 21, wherein said one or more gamma-radiation-sensitive materials comprises polytetrafluoroethylene (PTFE), fluorinated ethylene propylene (FEP), polyoxymethylene/polyacetals, aliphatic and amorphous grades of nylon polyamides, polymethylpentene, polypropylenes, or combinations thereof.

24. The single use in-line speed reduction torque-limiting assembly of claim 21, wherein said one or more gamma-radiation-sensitive materials are incorporated throughout said one or more non-metal gears as a wt/wt % of said gamma-radiation-sensitive material in all regions of said one or more non-metal gears.

25. The single use in-line speed reduction torque-limiting assembly of claim 21, wherein said one or more gamma-radiation-sensitive materials is incorporated in saidu one or more non-metal gears in a particular region of said one or more non-metal gears, while the remaining regions of said one or more non-metal gears are substantially free of any gamma-radiation-sensitive material, providing a desired wt/wt % for said one or more non-metal gears when considered as a whole.

26. The single use in-line speed reduction torque-limiting assembly of claim 25, wherein the wt/wt % of said one or more gamma-radiation-sensitive materials in said one or more non-metal gears is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

* * * * *